(12) United States Patent
Schenerman et al.

(10) Patent No.: US 7,608,260 B2
(45) Date of Patent: Oct. 27, 2009

(54) STABILIZED IMMUNOGLOBULINS

(75) Inventors: Mark A. Schenerman, Reisterstown, MD (US); Jose Casas-Finet, Gaithersburg, MD (US); Jinhua Feng, North Potomac, MD (US); Guillermo Tous, East Windsor, NJ (US)

(73) Assignee: MedImmune, LLC, Gaithersburg, MD (US)

( * ) Notice: Subject to any disclaimer, the term of this patent is extended or adjusted under 35 U.S.C. 154(b) by 470 days.

(21) Appl. No.: 10/751,744

(22) Filed: Jan. 5, 2004

(65) Prior Publication Data

US 2004/0191265 A1 Sep. 30, 2004

Related U.S. Application Data

(60) Provisional application No. 60/438,162, filed on Jan. 6, 2003.

(51) Int. Cl.
*A61K 39/00* (2006.01)
*A61K 39/38* (2006.01)
*A61K 39/395* (2006.01)

(52) U.S. Cl. .................................. 424/133.1; 424/130.1

(58) Field of Classification Search ....................... None
See application file for complete search history.

(56) References Cited

OTHER PUBLICATIONS

Bowie et al. (Science 1990, vol. 247, pp. 1306-1310.*
Xiang et al., Structural effect of recombinant monoclonal antibody on hinge region peptide bond hydrolysis, Journal of Chromatography B, 858 (2007), pp. 254-262.

* cited by examiner

*Primary Examiner*—Robert A Zeman

(57) ABSTRACT

The present invention provides stabilized immunoglobulin molecules that have increased storage stability and/or in vivo half-lives due to the mutation of one or more amino acids that would otherwise render the immunoglobulin molecules susceptible to degradation. In a preferred embodiment, the stabilized immunoglobulins of the invention have mutations at the heavy chain constant domain hinge region. Such stabilized immunoglobulin molecules, i.e., immunoglobulin molecules with increased storage stability have one or more of the following advantages they are more readily transported and/ storable for longer periods and/or less stringent conditions than non-stabilized counterparts; that smaller amounts and or less frequent dosing is required in the therapeutic, prophylactic or diagnostic use of such stabilized molecules.

12 Claims, 10 Drawing Sheets

Figure 11:
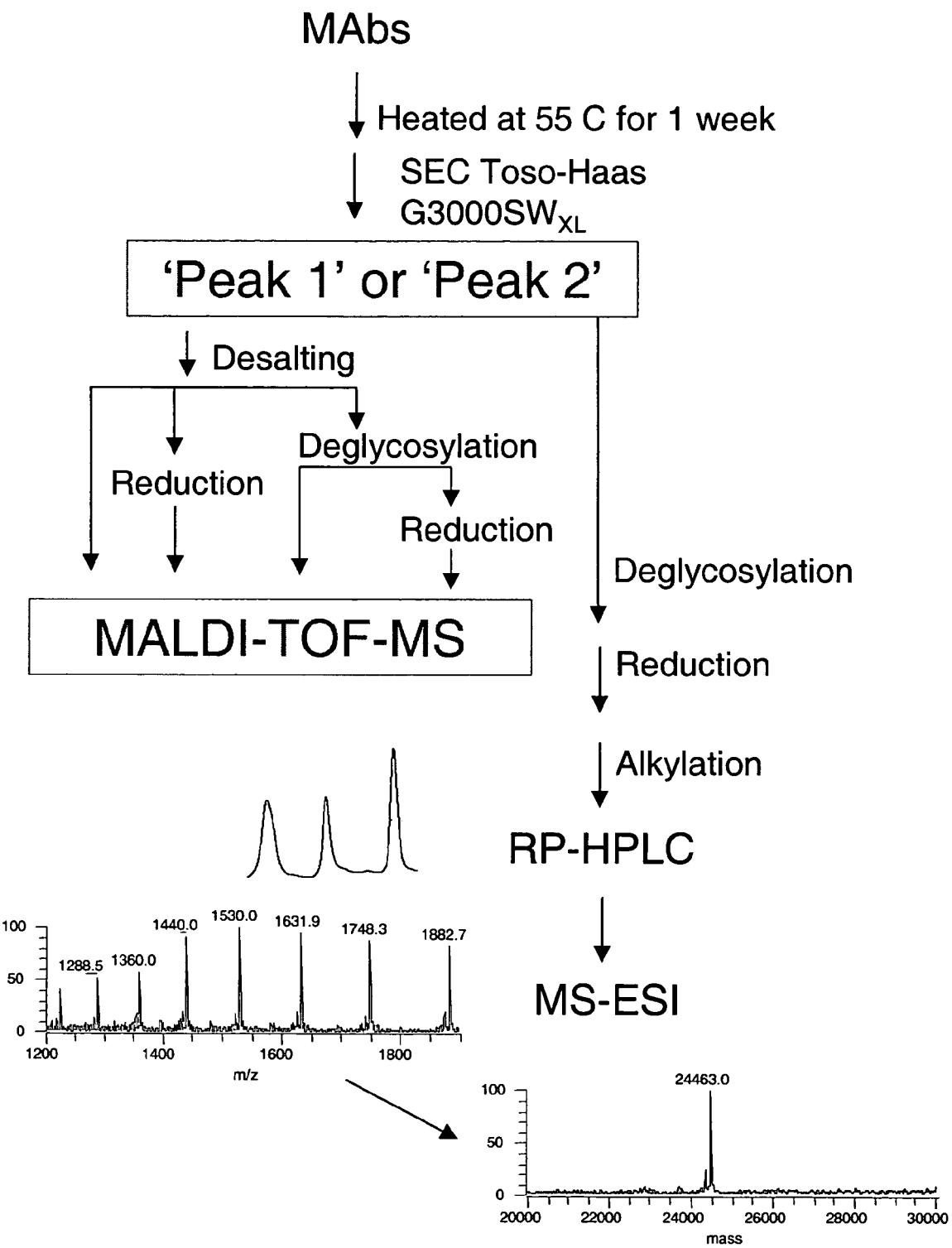

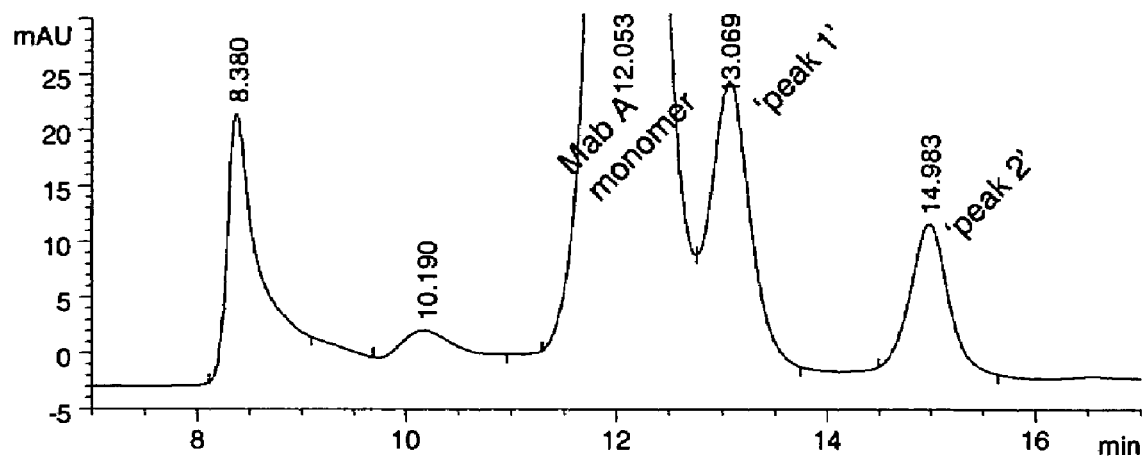
Figure 1: Size exclusion chromatography (SEC) of heat-stressed MAb A.

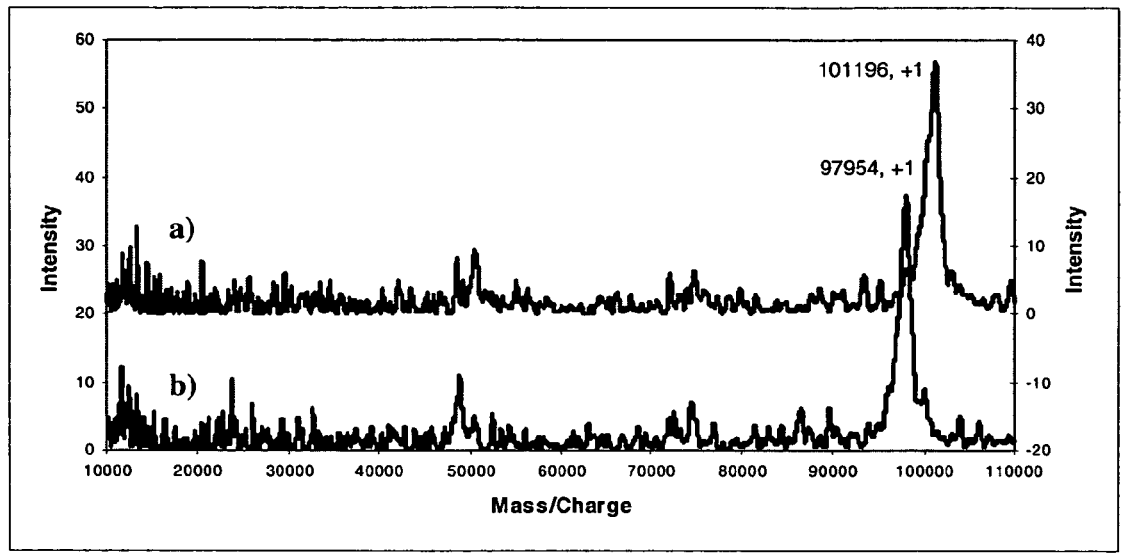
Figure 2: MALDI-TOF-MS mass spectra of a) non-deglycosylated and b) deglycosylated SEC fraction 'Peak 1' of the heat-stressed MAb A.
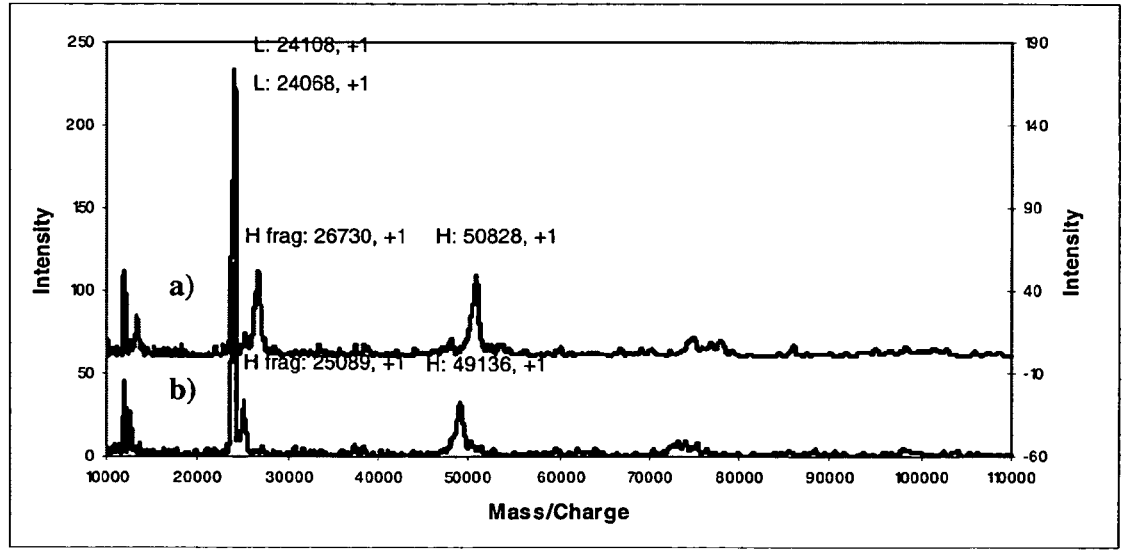
Figure 3: MALDI-TOF-MS mass spectra of a) non-deglycosylated and reduced and b) deglycosylated and reduced SEC fraction 'Peak 1' of the heat-stressed MAb A.

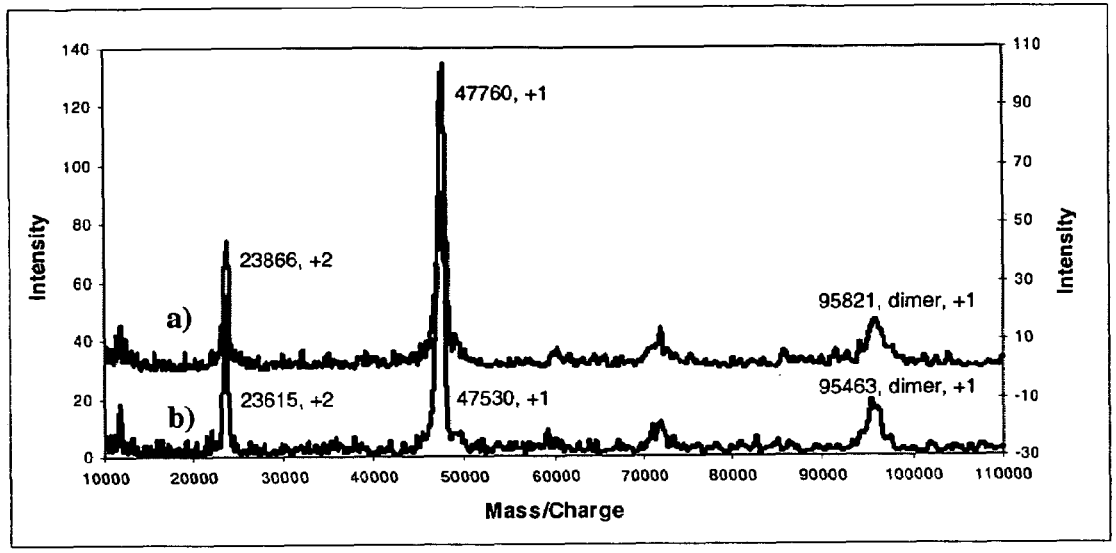
Figure 4: MALDI-TOF-MS mass spectra of a) non-deglycosylated and b) deglycosylated SEC fraction 'Peak 2' of the heat-stressed
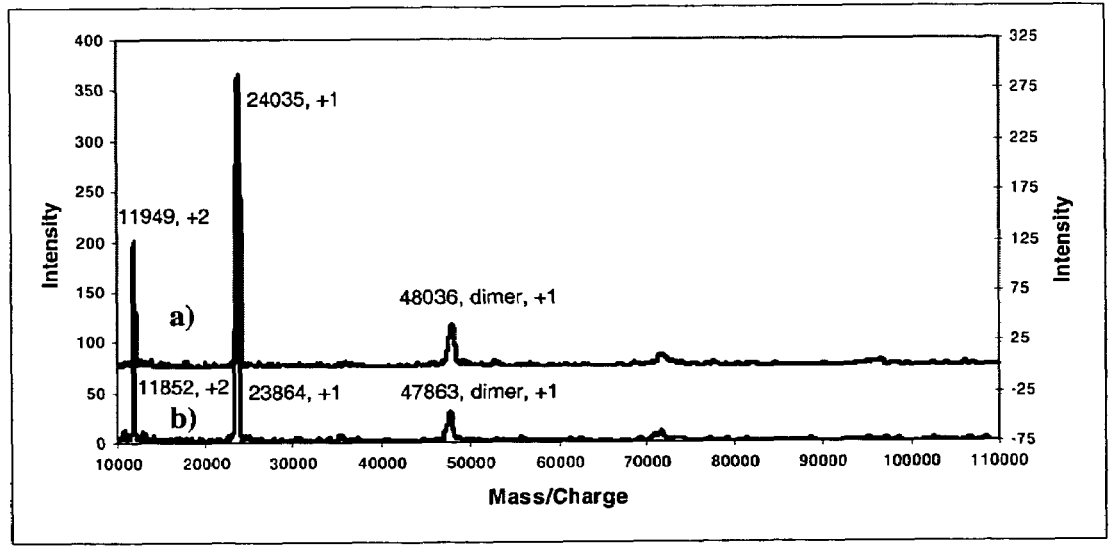
Figure 5: MALDI-TOF-MS mass spectra of a) non-deglycosylated and reduced and b) deglycosylated and reduced SEC fraction 'Peak 2' of the heat-stressed MAb A.

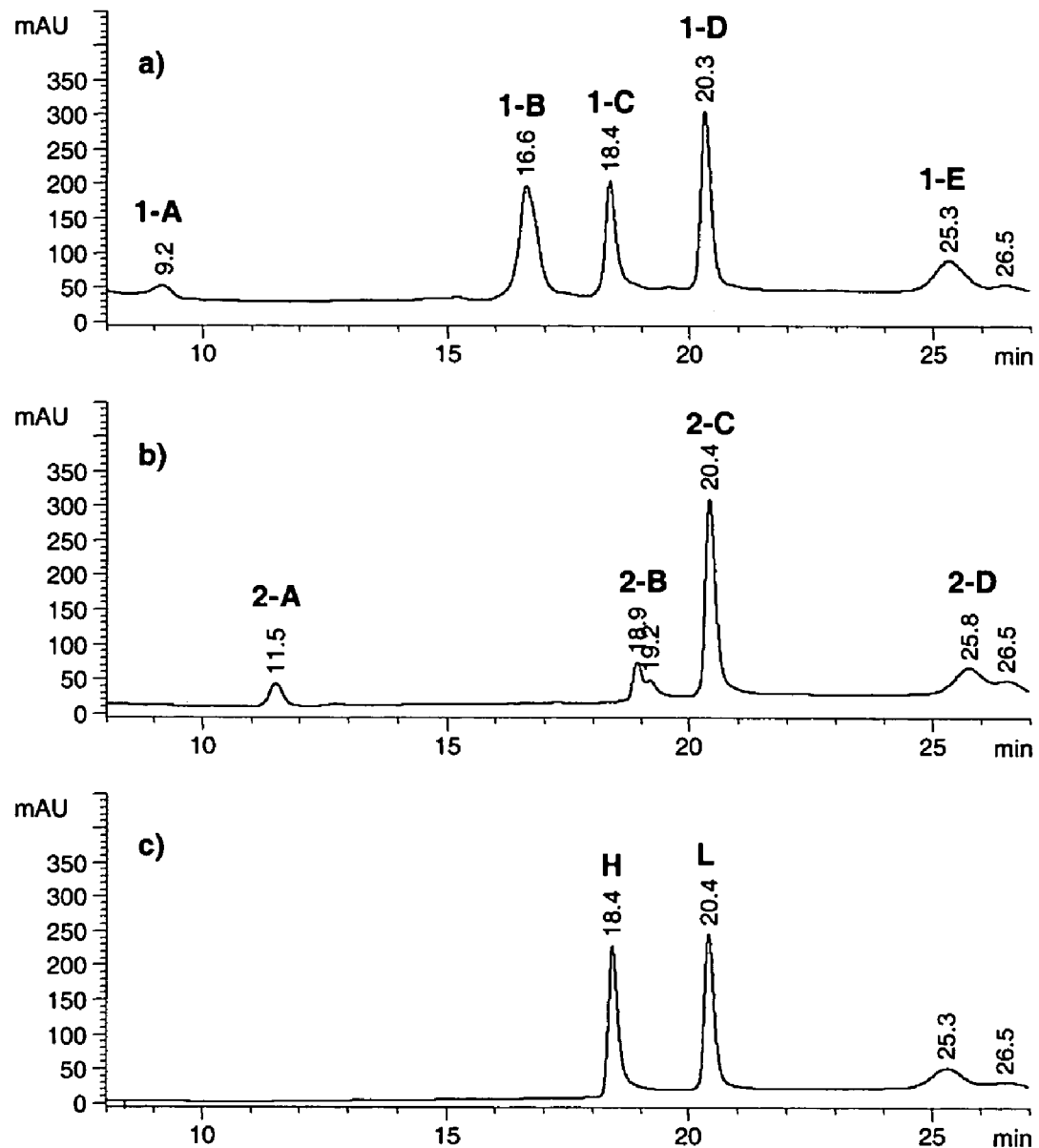
Figure 6: RP-HPLC chromatography for LC-ESI-MS analysis of deglycosylated, reduced, and alkylated: a) SEC fraction 'Peak 1', b) SEC fraction 'Peak 2', and c) non-heated reference standard of MAb A.

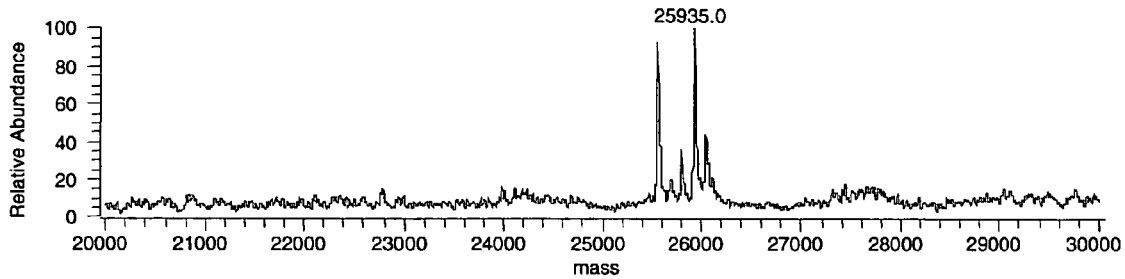
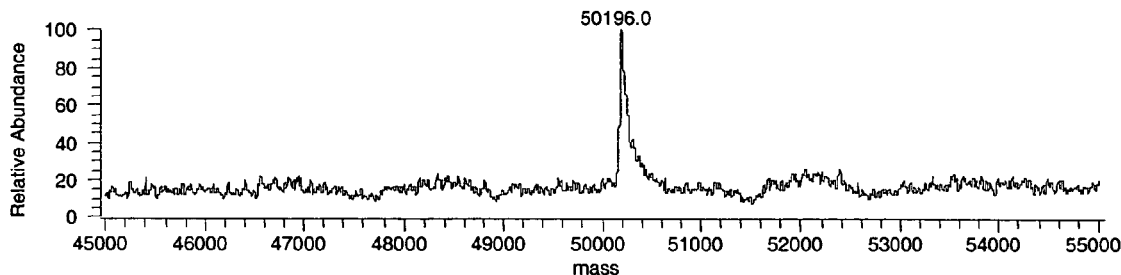
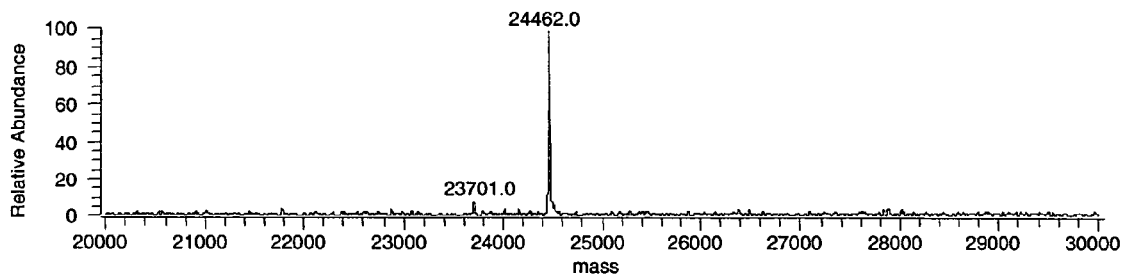
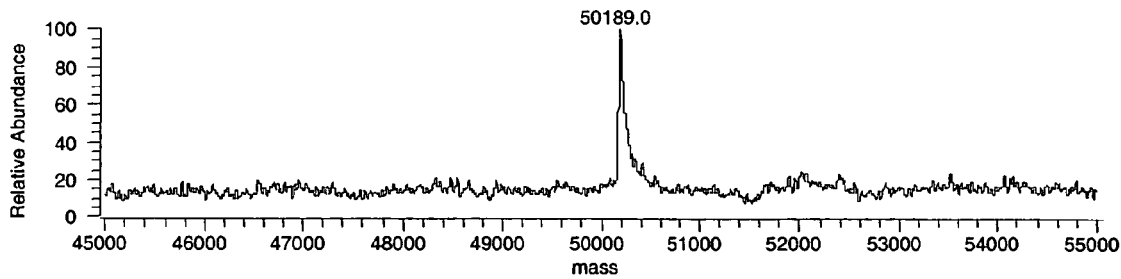
Figure 7: Reconstructed ESI-MS mass spectra for each peak a) 1-B, b) 1-C, c) 1-D, and d) 1-E shown in RP-HPLC chromatogram of deglycosylated, reduced, and alkylated SEC fraction 'Peak 1' of MAb A (Figure 6a).

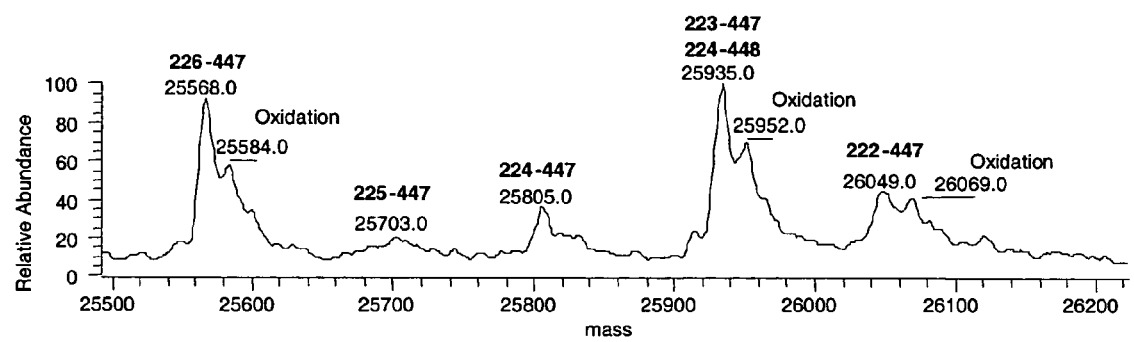
Figure 8: Expansion of the reconstructed mass spectrum shown in Figure 7a.

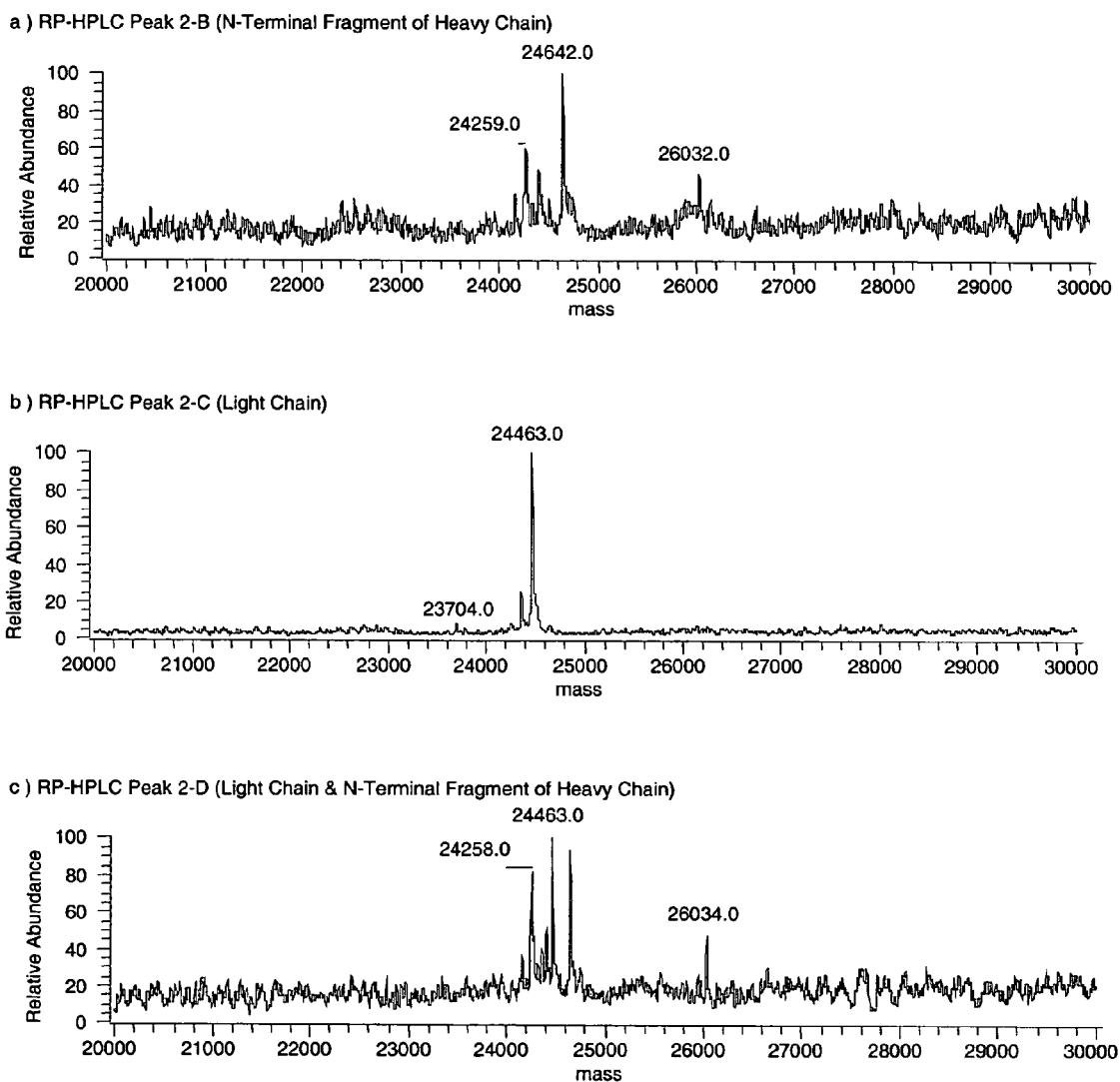
Figure 9: Reconstructed ESI-MS mass spectra for each peak a) 2-B, b) 2-C, and c) 2-D, shown in RP-HPLC chromatogram of deglycosylated, reduced, and alkylated SEC fraction 'Peak 2' of MAb A (Figure 6b).

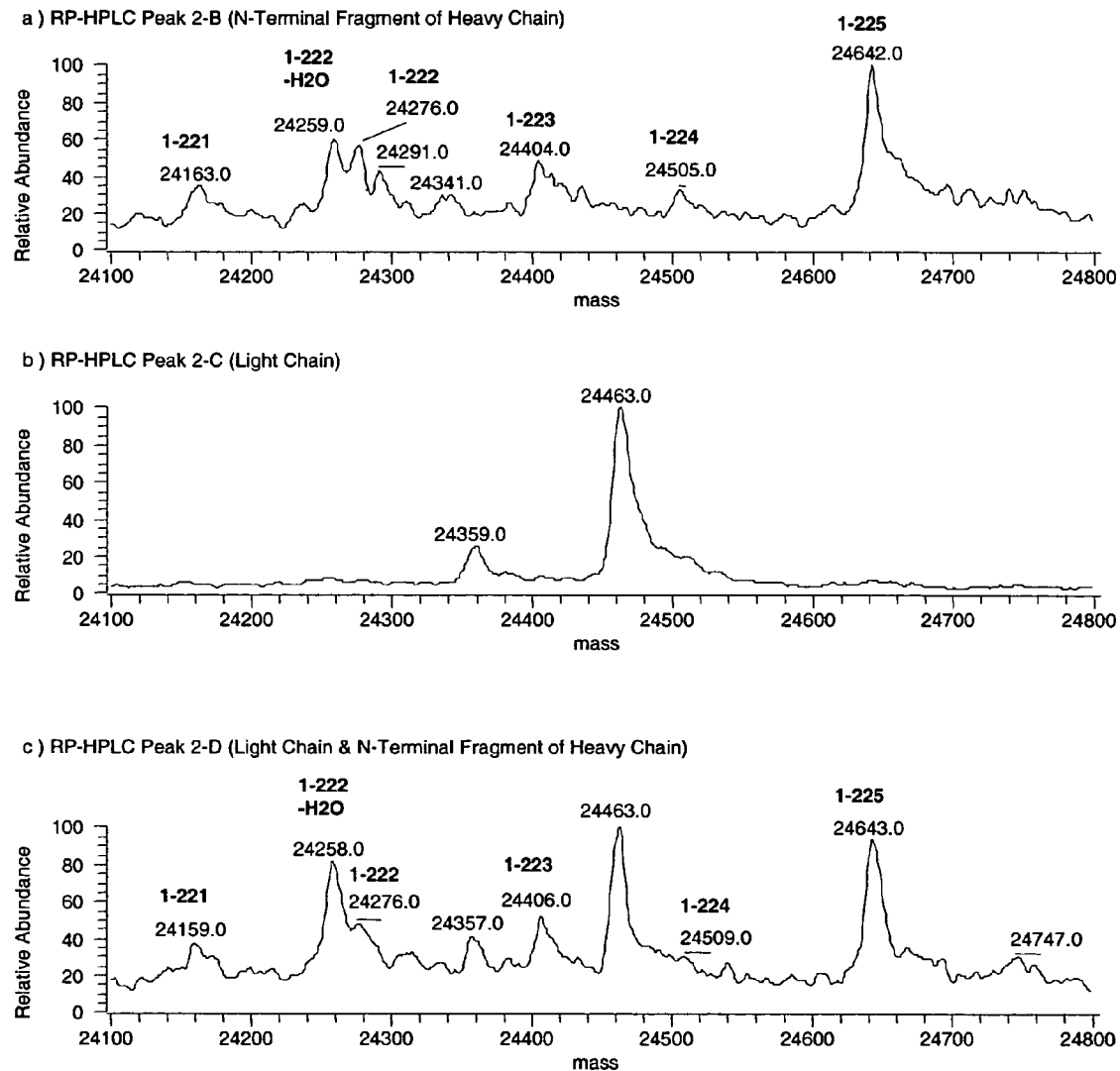
Figure 10: Expansion of the reconstructed mass spectra shown in Figure 9.

SEQUENCE LISTING

<160> NUMBER OF SEQ ID NOS: 79

<210> SEQ ID NO 1
<211> LENGTH: 7
<212> TYPE: PRT
<213> ORGANISM: Homo sapiens

<400> SEQUENCE: 1

Thr Ser Gly Met Ser Val Gly
1               5

<210> SEQ ID NO 2
<211> LENGTH: 16
<212> TYPE: PRT
<213> ORGANISM: Homo sapiens

```
<400> SEQUENCE: 2

Asp Ile Trp Trp Asp Asp Lys Lys Asp Tyr Asn Pro Ser Leu Lys Ser
1               5                   10                  15

<210> SEQ ID NO 3
<211> LENGTH: 10
<212> TYPE: PRT
<213> ORGANISM: Homo sapiens

<400> SEQUENCE: 3

Ser Met Ile Thr Asn Trp Tyr Phe Asp Val
1               5                   10

<210> SEQ ID NO 4
<211> LENGTH: 10
<212> TYPE: PRT
<213> ORGANISM: Homo sapiens

<400> SEQUENCE: 4

Lys Cys Gln Leu Ser Val Gly Tyr Met His
1               5                   10

<210> SEQ ID NO 5
<211> LENGTH: 7
<212> TYPE: PRT
<213> ORGANISM: Homo sapiens

<400> SEQUENCE: 5

Asp Thr Ser Lys Leu Ala Ser
1               5

<210> SEQ ID NO 6
<211> LENGTH: 9
<212> TYPE: PRT
<213> ORGANISM: Homo sapiens

<400> SEQUENCE: 6

Phe Gln Gly Ser Gly Tyr Pro Phe Thr
1               5

<210> SEQ ID NO 7
<211> LENGTH: 120
<212> TYPE: PRT
<213> ORGANISM: Homo sapiens

<400> SEQUENCE: 7

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
                100                 105                 110

Gly Thr Thr Val Thr Val Ser Ser
```

115                 120

<210> SEQ ID NO 8
<211> LENGTH: 106
<212> TYPE: PRT
<213> ORGANISM: Homo sapiens

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 9
<211> LENGTH: 120
<212> TYPE: PRT
<213> ORGANISM: Homo sapiens

<400> SEQUENCE: 9

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Phe Tyr Phe Asp Val Trp Gly Ala
            100                 105                 110

Gly Thr Thr Val Thr Val Ser Ser
        115                 120

<210> SEQ ID NO 10
<211> LENGTH: 7
<212> TYPE: PRT
<213> ORGANISM: Homo sapiens

<400> SEQUENCE: 10

Thr Ala Gly Met Ser Val Gly
1               5

<210> SEQ ID NO 11
<211> LENGTH: 106
<212> TYPE: PRT
<213> ORGANISM: Homo sapiens

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 12
<211> LENGTH: 10
<212> TYPE: PRT
<213> ORGANISM: Homo sapiens

<400> SEQUENCE: 12

Ser Met Ile Thr Asn Phe Tyr Phe Asp Val
1               5                   10

<210> SEQ ID NO 13
<211> LENGTH: 106
<212> TYPE: PRT
<213> ORGANISM: Homo sapiens

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Phe Ser Gly Tyr Pro Phe Thr
                85                  90                  95

Phe Gly Gly Gly Thr Lys Leu Glu Ile Lys
            100                 105

<210> SEQ ID NO 14
<211> LENGTH: 10
<212> TYPE: PRT
<213> ORGANISM: Homo sapiens

<400> SEQUENCE: 14

Ser Ala Ser Ser Ser Val Gly Tyr Met His
1               5                   10

<210> SEQ ID NO 15
<211> LENGTH: 7
<212> TYPE: PRT

<213> ORGANISM: Homo sapiens

<400> SEQUENCE: 15

Asp Thr Phe Lys Leu Ala Ser
1               5

<210> SEQ ID NO 16
<211> LENGTH: 9
<212> TYPE: PRT
<213> ORGANISM: Homo sapiens

<400> SEQUENCE: 16

Phe Gln Phe Ser Gly Tyr Pro Phe Thr
1               5

<210> SEQ ID NO 17
<211> LENGTH: 120
<212> TYPE: PRT
<213> ORGANISM: Homo sapiens

<400> SEQUENCE: 17

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Ala
            100                 105                 110

Gly Thr Thr Val Thr Val Ser Ser
        115                 120

<210> SEQ ID NO 18
<211> LENGTH: 7
<212> TYPE: PRT
<213> ORGANISM: Homo sapiens

<400> SEQUENCE: 18

Thr Pro Gly Met Ser Val Gly
1               5

<210> SEQ ID NO 19
<211> LENGTH: 16
<212> TYPE: PRT
<213> ORGANISM: Homo sapiens

<400> SEQUENCE: 19

Asp Ile Trp Trp Asp Asp Lys Lys His Tyr Asn Pro Ser Leu Lys Asp
1               5                   10                  15

<210> SEQ ID NO 20
<211> LENGTH: 10
<212> TYPE: PRT
<213> ORGANISM: Homo sapiens

<400> SEQUENCE: 20

```
Asp Met Ile Phe Asn Phe Tyr Phe Asp Val
1               5                   10
```

<210> SEQ ID NO 21
<211> LENGTH: 106
<212> TYPE: PRT
<213> ORGANISM: Homo sapiens

<400> SEQUENCE: 21

```
Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
                20                  25                  30

His Trp Tyr Gln Gln Lys Pro Gly Lys Ala Pro Lys Leu Leu Ile Tyr
        35                  40                  45

Asp Thr Phe Tyr Leu Ser Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105
```

<210> SEQ ID NO 22
<211> LENGTH: 10
<212> TYPE: PRT
<213> ORGANISM: Homo sapiens

<400> SEQUENCE: 22

```
Ser Leu Ser Ser Arg Val Gly Tyr Met His
1               5                   10
```

<210> SEQ ID NO 23
<211> LENGTH: 7
<212> TYPE: PRT
<213> ORGANISM: Homo sapiens

<400> SEQUENCE: 23

```
Asp Thr Phe Tyr Leu Ser Ser
1               5
```

<210> SEQ ID NO 24
<211> LENGTH: 120
<212> TYPE: PRT
<213> ORGANISM: Homo sapiens

<400> SEQUENCE: 24

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
                20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys His Tyr Asn Pro Ser
        50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
```

```
                    85                  90                  95
Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 25
<211> LENGTH: 16
<212> TYPE: PRT
<213> ORGANISM: Homo sapiens

<400> SEQUENCE: 25

Asp Ile Trp Trp Asp Gly Lys Lys His Tyr Asn Pro Ser Leu Lys Asp
1               5                   10                  15

<210> SEQ ID NO 26
<211> LENGTH: 106
<212> TYPE: PRT
<213> ORGANISM: Homo sapiens

<400> SEQUENCE: 26

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Arg Gly Leu Pro Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 27
<211> LENGTH: 7
<212> TYPE: PRT
<213> ORGANISM: Homo sapiens

<400> SEQUENCE: 27

Asp Thr Arg Gly Leu Pro Ser
1               5

<210> SEQ ID NO 28
<211> LENGTH: 120
<212> TYPE: PRT
<213> ORGANISM: Homo sapiens

<400> SEQUENCE: 28

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
    50                  55                  60
```

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 29
<211> LENGTH: 10
<212> TYPE: PRT
<213> ORGANISM: Homo sapiens

<400> SEQUENCE: 29

Asp Met Ile Phe Asn Trp Tyr Phe Asp Val
1               5                   10

<210> SEQ ID NO 30
<211> LENGTH: 106
<212> TYPE: PRT
<213> ORGANISM: Homo sapiens

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Ser Pro Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Met Arg Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 31
<211> LENGTH: 10
<212> TYPE: PRT
<213> ORGANISM: Homo sapiens

<400> SEQUENCE: 31

Ser Pro Ser Ser Arg Val Gly Tyr Met His
1               5                   10

<210> SEQ ID NO 32
<211> LENGTH: 7
<212> TYPE: PRT
<213> ORGANISM: Homo sapiens

<400> SEQUENCE: 32

Asp Thr Met Arg Leu Ala Ser
1               5

<210> SEQ ID NO 33
<211> LENGTH: 120
<212> TYPE: PRT
<213> ORGANISM: Homo sapiens

<400> SEQUENCE: 33

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Pro
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Gly Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
        115                 120

<210> SEQ ID NO 34
<211> LENGTH: 106
<212> TYPE: PRT
<213> ORGANISM: Homo sapiens

<400> SEQUENCE: 34

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 35
<211> LENGTH: 7
<212> TYPE: PRT
<213> ORGANISM: Homo sapiens

<400> SEQUENCE: 35

Asp Thr Phe Lys Leu Ser Ser
1               5

<210> SEQ ID NO 36
<211> LENGTH: 120
<212> TYPE: PRT
<213> ORGANISM: Homo sapiens

<400> SEQUENCE: 36

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala

```
                    20                  25                  30
Gly Met Ser Val Gly Trp Ile Arg Gln Pro Gly Lys Ala Leu Glu
                35                  40                  45

Trp Leu Ala Asp Ile Trp Trp Asp Gly Lys Lys Asp Tyr Asn Pro Ser
 50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
                100                 105                 110

Gly Thr Thr Val Thr Val Ser Ser
        115                 120

<210> SEQ ID NO 37
<211> LENGTH: 16
<212> TYPE: PRT
<213> ORGANISM: Homo sapiens

<400> SEQUENCE: 37

Asp Ile Trp Trp Asp Gly Lys Lys Asp Tyr Asn Pro Ser Leu Lys Asp
1               5                   10                  15

<210> SEQ ID NO 38
<211> LENGTH: 106
<212> TYPE: PRT
<213> ORGANISM: Homo sapiens

<400> SEQUENCE: 38

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
                20                  25                  30

His Trp Tyr Gln Gln Lys Pro Gly Lys Ala Pro Lys Leu Leu Ile Tyr
                35                  40                  45

Asp Thr Phe Lys Leu Ser Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
                100                 105

<210> SEQ ID NO 39
<211> LENGTH: 10
<212> TYPE: PRT
<213> ORGANISM: Homo sapiens

<400> SEQUENCE: 39

Ser Ala Ser Ser Arg Val Gly Tyr Met His
1               5                   10

<210> SEQ ID NO 40
<211> LENGTH: 120
<212> TYPE: PRT
<213> ORGANISM: Homo sapiens

<400> SEQUENCE: 40
```

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Gly Lys Lys Ser Tyr Asn Pro Ser
50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
            115                 120

<210> SEQ ID NO 41
<211> LENGTH: 16
<212> TYPE: PRT
<213> ORGANISM: Homo sapiens

<400> SEQUENCE: 41

Asp Ile Trp Trp Asp Gly Lys Lys Ser Tyr Asn Pro Ser Leu Lys Asp
1               5                   10                  15

<210> SEQ ID NO 42
<211> LENGTH: 106
<212> TYPE: PRT
<213> ORGANISM: Homo sapiens

<400> SEQUENCE: 42

Asp Ile Gln Met Thr Gln Ser Pro Ser Thr Leu Ser Ala Ser Val Gly
1               5                   10                  15

Asp Arg Val Thr Ile Thr Cys Ser Leu Ser Ser Arg Val Gly Tyr Met
                20                  25                  30

His Trp Tyr Gln Gln Lys Pro Gly Lys Ala Pro Lys Leu Leu Ile Tyr
            35                  40                  45

Asp Thr Met Tyr Gln Ser Ser Gly Val Pro Ser Arg Phe Ser Gly Ser
            50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 43
<211> LENGTH: 7
<212> TYPE: PRT
<213> ORGANISM: Homo sapiens

<400> SEQUENCE: 43

Asp Thr Met Tyr Gln Ser Ser
1               5

<210> SEQ ID NO 44
<211> LENGTH: 112
<212> TYPE: PRT

<213> ORGANISM: Homo sapiens

<400> SEQUENCE: 44

```
Gln Val Thr Leu Arg Glu Ser Gly Pro Ala Leu Val Lys Pro Thr Gln
1               5                   10                  15
Thr Leu Thr Leu Thr Cys Thr Phe Ser Gly Phe Ser Leu Ser Thr Ala
            20                  25                  30
Gly Met Ser Val Gly Trp Ile Arg Gln Pro Pro Gly Lys Ala Leu Glu
        35                  40                  45
Trp Leu Ala Asp Ile Trp Trp Asp Gly Lys Lys Ser Tyr Asn Pro Ser
    50                  55                  60
Leu Lys Asp Arg Leu Thr Ile Ser Lys Asp Thr Ser Lys Asn Gln Val
65                  70                  75                  80
Val Leu Lys Val Thr Asn Met Asp Pro Ala Asp Thr Ala Thr Tyr Tyr
                85                  90                  95
Cys Ala Arg Asp Met Ile Phe Asn Phe Tyr Phe Asp Val Trp Gly Gln
            100                 105                 110
```

<210> SEQ ID NO 45
<211> LENGTH: 16
<212> TYPE: PRT
<213> ORGANISM: Homo sapiens

<400> SEQUENCE: 45

```
Asp Ile Trp Trp Asp Asp Lys Lys Ser Tyr Asn Pro Ser Leu Lys Asp
1               5                   10                  15
```

<210> SEQ ID NO 46
<211> LENGTH: 106
<212> TYPE: PRT
<213> ORGANISM: Homo sapiens

<400> SEQUENCE: 46

```
Asp Ile Gln Met Thr Gln Ser Pro Ser Thr Leu Ser Ala Ser Val Gly
1               5                   10                  15
Asp Arg Val Thr Ile Thr Cys Leu Pro Ser Ser Arg Val Gly Tyr Met
            20                  25                  30
His Trp Tyr Gln Gln Lys Pro Gly Lys Ala Pro Lys Leu Leu Ile Tyr
        35                  40                  45
Asp Thr Met Tyr Gln Ala Ser Gly Val Pro Ser Arg Phe Ser Gly Ser
    50                  55                  60
Gly Ser Gly Thr Glu Phe Thr Leu Thr Ile Ser Ser Leu Gln Pro Asp
65                  70                  75                  80
Asp Phe Ala Thr Tyr Tyr Cys Phe Gln Phe Ser Gly Tyr Pro Phe Thr
                85                  90                  95
Phe Gly Gly Gly Thr Lys Leu Glu Ile Lys
            100                 105
```

<210> SEQ ID NO 47
<211> LENGTH: 10
<212> TYPE: PRT
<213> ORGANISM: Homo sapiens

<400> SEQUENCE: 47

```
Leu Pro Ser Ser Arg Val Gly Tyr Met His
1               5                   10
```

<210> SEQ ID NO 48
<211> LENGTH: 120

```
<212> TYPE: PRT
<213> ORGANISM: Homo sapiens

<400> SEQUENCE: 48

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120

<210> SEQ ID NO 49
<211> LENGTH: 106
<212> TYPE: PRT
<213> ORGANISM: Homo sapiens

<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Phe Phe Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 50
<211> LENGTH: 7
<212> TYPE: PRT
<213> ORGANISM: Homo sapiens

<400> SEQUENCE: 50

Asp Thr Phe Phe Leu Asp Ser
1               5

<210> SEQ ID NO 51
<211> LENGTH: 120
<212> TYPE: PRT
<213> ORGANISM: Homo sapiens

<400> SEQUENCE: 51

Gln Val Thr Leu Arg Glu Ser Gly Pro Ala Leu Val Lys Pro Thr Gln
1               5                   10                  15
```

```
Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Ser Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Trp Tyr Phe Asp Val Trp Gly Gln
            100                 105                 110

Gly Thr Thr Val Thr Val Ser Ser
            115                 120

<210> SEQ ID NO 52
<211> LENGTH: 106
<212> TYPE: PRT
<213> ORGANISM: Homo sapiens

<400> SEQUENCE: 52

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Arg Tyr Gln Ser Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 53
<211> LENGTH: 7
<212> TYPE: PRT
<213> ORGANISM: Homo sapiens

<400> SEQUENCE: 53

Asp Thr Arg Tyr Gln Ser Ser
1               5

<210> SEQ ID NO 54
<211> LENGTH: 106
<212> TYPE: PRT
<213> ORGANISM: Homo sapiens

<400> SEQUENCE: 54

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45
```

```
Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 55
<211> LENGTH: 120
<212> TYPE: PRT
<213> ORGANISM: Homo sapiens

<400> SEQUENCE: 55

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
                 20                  25                  30

Gly Met Ser Val Gly Trp Ile Arg Gln Pro Pro Gly Lys Ala Leu Glu
             35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Asp Met Ile Phe Asn Trp Tyr Phe Asp Val Trp Gly Ala
            100                 105                 110

Gly Thr Thr Val Thr Val Ser Ser
            115                 120

<210> SEQ ID NO 56
<211> LENGTH: 106
<212> TYPE: PRT
<213> ORGANISM: Homo sapiens

<400> SEQUENCE: 56

Asp Ile Gln Met Thr Gln Ser Pro Ser Thr Leu Ser Ala Ser Val Gly
  1               5                  10                  15

Asp Arg Val Thr Ile Thr Cys Ser Ala Ser Ser Ser Val Gly Tyr Met
                 20                  25                  30

His Trp Tyr Gln Gln Lys Pro Gly Lys Ala Pro Lys Leu Leu Ile Tyr
             35                  40                  45

Asp Thr Phe Lys Leu Ala Ser Gly Val Pro Ser Arg Phe Ser Gly Ser
 50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 57
<211> LENGTH: 106
<212> TYPE: PRT
<213> ORGANISM: Homo sapiens
```

```
<400> SEQUENCE: 57

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Phe Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 58
<211> LENGTH: 7
<212> TYPE: PRT
<213> ORGANISM: Homo sapiens

<400> SEQUENCE: 58

Asp Thr Tyr Lys Gln Thr Ser
1               5

<210> SEQ ID NO 59
<211> LENGTH: 106
<212> TYPE: PRT
<213> ORGANISM: Homo sapiens

<400> SEQUENCE: 59

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Arg Tyr Leu Ser Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 60
<211> LENGTH: 106
<212> TYPE: PRT
<213> ORGANISM: Homo sapiens

<400> SEQUENCE: 60

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
            35                  40                  45
```

Asp Thr Phe Lys Leu Ala Ser Gly Val Pro Ser Arg Phe Ser Gly Ser
         50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Phe Tyr Pro Phe Thr
                 85                  90                  95

Phe Gly Gly Gly Thr Lys Leu Glu Ile Lys
            100                 105

<210> SEQ ID NO 61
<211> LENGTH: 9
<212> TYPE: PRT
<213> ORGANISM: Homo sapiens

<400> SEQUENCE: 61

Phe Gln Gly Ser Phe Tyr Pro Phe Thr
1               5

<210> SEQ ID NO 62
<211> LENGTH: 106
<212> TYPE: PRT
<213> ORGANISM: Homo sapiens

<400> SEQUENCE: 62

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
             20                  25                  30

His Trp Tyr Gln Gln Lys Pro Gly Lys Ala Pro Lys Leu Leu Ile Tyr
             35                  40                  45

Asp Thr Phe Lys Leu Thr Ser Gly Val Pro Ser Arg Phe Ser Gly Ser
         50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 63
<211> LENGTH: 7
<212> TYPE: PRT
<213> ORGANISM: Homo sapiens

<400> SEQUENCE: 63

Asp Thr Phe Lys Leu Thr Ser
1               5

<210> SEQ ID NO 64
<211> LENGTH: 106
<212> TYPE: PRT
<213> ORGANISM: Homo sapiens

<400> SEQUENCE: 64

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
             20                  25                  30

His Trp Tyr Gln Gln Lys Pro Gly Lys Ala Pro Lys Leu Leu Ile Tyr

```
                 35                  40                  45
Asp Thr Phe Arg Leu Ala Ser Gly Val Pro Ser Arg Phe Ser Gly Ser
             50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
                100                 105

<210> SEQ ID NO 65
<211> LENGTH: 106
<212> TYPE: PRT
<213> ORGANISM: Homo sapiens

<400> SEQUENCE: 65

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Ser Val Gly Tyr Met
             20                  25                  30

His Trp Tyr Gln Gln Lys Pro Gly Lys Ala Pro Lys Leu Leu Ile Tyr
         35                  40                  45

Asp Thr Phe Arg Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
                100                 105

<210> SEQ ID NO 66
<211> LENGTH: 7
<212> TYPE: PRT
<213> ORGANISM: Homo sapiens

<400> SEQUENCE: 66

Asp Thr Phe Arg Leu Ala Ser
 1               5

<210> SEQ ID NO 67
<211> LENGTH: 120
<212> TYPE: PRT
<213> ORGANISM: Homo sapiens

<400> SEQUENCE: 67

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ala
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys His Tyr Asn Pro Ser
     50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95
```

```
Cys Ala Arg Asp Met Ile Phe Asn Trp Tyr Phe Asp Val Trp Gly Ala
            100                 105                 110

Gly Thr Thr Val Thr Val Ser Ser
        115                 120

<210> SEQ ID NO 68
<211> LENGTH: 106
<212> TYPE: PRT
<213> ORGANISM: Homo sapiens

<400> SEQUENCE: 68

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Tyr Arg His Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 69
<211> LENGTH: 7
<212> TYPE: PRT
<213> ORGANISM: Homo sapiens

<400> SEQUENCE: 69

Asp Thr Tyr Arg His Ser Ser
1               5

<210> SEQ ID NO 70
<211> LENGTH: 106
<212> TYPE: PRT
<213> ORGANISM: Homo sapiens

<400> SEQUENCE: 70

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Tyr Lys Gln Thr Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 71
<211> LENGTH: 106
```

```
<212> TYPE: PRT
<213> ORGANISM: Homo sapiens

<400> SEQUENCE: 71

Asp Ile Gln Met Thr Gln Ser Pro Ser Thr Leu Ser Ala Ser Val Gly
 1               5                  10                  15

Asp Arg Val Thr Ile Thr Cys Ser Leu Ser Ser Val Gly Tyr Met
             20                  25                  30

His Trp Tyr Gln Gln Lys Pro Gly Lys Ala Pro Lys Leu Leu Ile Tyr
         35                  40                  45

Asp Thr Phe Phe His Arg Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 72
<211> LENGTH: 10
<212> TYPE: PRT
<213> ORGANISM: Homo sapiens

<400> SEQUENCE: 72

Ser Leu Ser Ser Ser Val Gly Tyr Met His
 1               5                  10

<210> SEQ ID NO 73
<211> LENGTH: 7
<212> TYPE: PRT
<213> ORGANISM: Homo sapiens

<400> SEQUENCE: 73

Asp Thr Phe Phe His Arg Ser
 1               5

<210> SEQ ID NO 74
<211> LENGTH: 106
<212> TYPE: PRT
<213> ORGANISM: Homo sapiens

<400> SEQUENCE: 74

Asp Ile Gln Met Thr Gln Ser Pro Ser Thr Leu Ser Ala Ser Val Gly
 1               5                  10                  15

Asp Arg Val Thr Ile Thr Cys Ser Ala Ser Ser Arg Val Gly Tyr Met
             20                  25                  30

His Trp Tyr Gln Gln Lys Pro Gly Lys Ala Pro Lys Leu Leu Ile Tyr
         35                  40                  45

Asp Thr Leu Leu Leu Asp Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys
            100                 105

<210> SEQ ID NO 75
```

```
<211> LENGTH: 7
<212> TYPE: PRT
<213> ORGANISM: Homo sapiens

<400> SEQUENCE: 75

Asp Thr Leu Leu Leu Asp Ser
1               5

<210> SEQ ID NO 76
<211> LENGTH: 106
<212> TYPE: PRT
<213> ORGANISM: Homo sapiens

<400> SEQUENCE: 76

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Phe Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105

<210> SEQ ID NO 77
<211> LENGTH: 7
<212> TYPE: PRT
<213> ORGANISM: Homo sapiens

<400> SEQUENCE: 77

Asp Thr Ser Phe Leu Asp Ser
1               5

<210> SEQ ID NO 78
<211> LENGTH: 120
<212> TYPE: PRT
<213> ORGANISM: Homo sapiens

<400> SEQUENCE: 78

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Thr Asn Phe Tyr Phe Asp Val Trp Gly Ala
            100                 105                 110

Gly Thr Thr Val Thr Val Ser Ser
```

```
<210> SEQ ID NO 79
<211> LENGTH: 10
<212> TYPE: PRT
<213> ORGANISM: Homo sapiens

<400> SEQUENCE: 79

Asp Met Ile Thr Asn Phe Tyr Phe Asp Val
1               5                   10
```

US 7,608,260 B2

STABILIZED IMMUNOGLOBULINS

This application is entitled to the benefit and claims priority under 35 U.S.C. § 119(e) to U.S. Provisional Application Ser. No. 60/438,162, filed Jan. 6, 2003, which is incorporated herein by reference in its entirety.

1. INTRODUCTION

The present invention relates to modified glycoprotein molecules, including modified immunoglobulin molecules, with improved stability. Specifically, these immunoglobulin molecules have amino acid modifications that render the constant domain hinge region less susceptible to degradation. The improved stability of the modified immunoglobulin molecules can lead to increased storage stability and/or increased half-life following administration to a subject. The present invention further relates to mass-spectrometric methods of identifying glycoprotein, for example immunoglobulin, degradation products and method of designing stabilized glycoprotein molecules, such as immunoglobulin molecules, with increased stability based on the identification of degradation products by the methods of the present invention.

2. BACKGROUND OF THE INVENTION

The use of immunoglobulins as therapeutic agents has increased dramatically in recent years and have expanded to different areas of medical treatments. Such uses include treatment of agammaglobulinemia and hypogammaglobulinemia, as immunosuppressive agents for treating autoimmune diseases and graft-vs.-host (GVH) diseases, the treatment of lymphoid malignancies, and passive immunotherapies for the treatment of various systemic and infectious diseases. Also, immunoglobulins are useful as in vivo diagnostic tools, for example, in diagnostic imaging procedures.

One critical issue in these therapies is the persistence of immunoglobulins in the circulation. The rate of immunoglobulin clearance directly affects the amount and frequency of dosage of the immunoglobulin. Increased dosage and frequency of dosage may cause adverse effects in the patient and also increase medical costs. Further, immunoglobulin preparations often have short shelf lives and may lose biological activity of the antibodies resulting from chemical and physical instabilities during the storage and shipment, which decreases the effectiveness of these molecules and results in manufacturing waste.

Thus, there is in a need in the pharmaceutical industry for immunoglobulin molecules with increased storage stability and/or increased in vivo half-lives.

3. SUMMARY OF THE INVENTION

The present invention is based upon the inventors' development of a novel method of analyzing and identifying glycoprotein (including but not limited to immunoglobulin) degradation products. The identification of the boundaries of glycoprotein degradation product identifies amino acid residues within the corresponding glycoprotein that destabilize that glycoprotein, rendering it susceptible to degradation.

Using the methods described herein, the present inventors have identified a portion of the hinge region of the human heavy chain IgG1 constant domain as a site of immunoglobulin degradation. Methods of screening for and identifying point mutations within this hinge region portion that render the hinge region less susceptible to degradation are provided. Such methods lead to the identification and production of stabilized immunoglobulin molecules with increased storage stability and/or serum half life. Increasing the half-life of therapeutic and diagnostic immunoglobulin molecules using methods of the invention has many benefits including, for example, longer term storage, storage under less stringent conditions, reducing the amount and/or frequency of dosing of these stabilized immunoglobulin molecules, for example, in vaccines, passive immunotherapy and other therapeutic and prophylactic methods.

Thus, the present invention relates to a stabilized immunoglobulin molecule that has an increased storage stability by virtue of the presence of a modified IgG constant domain hinge region, wherein the IgG constant domain is modified (e.g., by amino acid substitution, deletion or insertion) to reduce the susceptibility of the molecule to degradation. In a particular embodiment, the present invention relates to modified IgGs, whose storage stability and/or in vivo half-lives are extended by the modification of labile amino acid residues in the hinge region of the heavy chain constant domain of an immunoglobulin molecule. In a preferred embodiment, the stabilized immunoglobulin region is modified by making point mutations in labile amino acids (e.g., histidine or threonine) or reactive amino acids (e.g., lysine or glutamic acid) in the upper hinge portion (human IgG1 residues 226-243 and corresponding residues in other IgG subtypes and/or immunoglobulins from other species) and/or in the flanking CH1 and/or CH2 sequences (human IgG1 residue 249 and corresponding residues in other IgG subtypes and/or immunoglobulins from other species). In a preferred mode of the embodiment, the labile or reactive amino acids are substituted with bulky inactive amino acids (e.g., valine or isoleucine). The invention also relates to other types of immunoglobulins or fragments thereof (i.e., non-IgG immunoglobulins such as IgA, IgE and IgM) that are similarly modified in regions corresponding to the IgG upper hinge regions. Such modifications may also alter (i.e., increase or decrease) the bioavailability (e.g., transport to mucosal surfaces, or other target tissues) of the molecules.

Accordingly, in certain specific embodiments, the present invention provides a modified IgG comprising a modified hinge region containing one or more amino acid modifications at a position corresponding to from position 233 to position 239 of human IgG1 relative to a corresponding wild-type hinge region and/or an amino acid modification at a residue corresponding to position 249 of a human IgG1 heavy chain, said modified IgG exhibiting reduced degradation of said modified IgG upon heating to 55° C. for one week than a corresponding IgG not comprising said one or more amino acid modifications. Nucleic acids, preferably isolated nucleic acids, encoding the foregoing modified IgG molecules, as well as vectors comprising such nucleic acids, are also provided. Additionally, the present invention provides host cells, for example a mammalian cell, more preferably a mammalian myeloma cell, comprising a nucleic acid comprising a nucleotide sequence encoding a modified IgG of the invention operably linked to a promoter. Methods of producing the modified IgG of the invention by culturing a host cell for example a mammalian cell, more preferably a mammalian myeloma cell, comprising a nucleic acid, which nucleic acid comprises a nucleotide sequence encoding a modified IgG of the invention operably linked to a promoter, under conditions appropriate for the expression of said IgG, are also provided. Such methods may further entail isolating said modified IgG.

In specific embodiments, the invention provides immunoglobulins or other bioactive molecules that contain an IgG1 heavy chain hinge domain (preferably human) having an amino acid modification at histidine 237, more specifically is substituted at histidine 237. In certain embodiments, histidine 237 is substituted with valine or isoleucine.

In other specific embodiments, the invention provides immunoglobulins or other bioactive molecules that contain an IgG1 CH2 domain having an amino acid modification at glycine 249, more specifically is substituted at glycine 249. In certain embodiments, glycine 249 is substituted with valine or isoleucine.

Additionally, methods of increasing the stability of glycoproteins, more preferably of immunoglobulins, are provided. In certain embodiments, the immunoglobulin is an IgG. Accordingly, in certain embodiments, the present invention provides a method for increasing the stability of an IgG, said method comprising introducing one or more amino acid modifications in the hinge region of said IgG at a position corresponding to from position 233 to position 239 of human IgG1 and/or an amino acid modification at a residue corresponding to position 249 of a human IgG1 heavy chain, which one or more modifications result in reduced degradation of said IgG upon heating to 55° C. for one week than a corresponding IgG not comprising said one or more amino acid modifications.

Additionally, the present invention provides methods of identifying amino acid residues in glycoproteins that render the glycoproteins susceptible to degradation. These methods can also be used to screen for a modified immunoglobulin with increased stability. Thus, in certain specific embodiments, the present invention provides methods of identifying amino acid residues in glycoproteins that render the glycoproteins susceptible to degradation, said methods comprising:(a) heating the glycoprotein at 55° C. for a week; (b) fractionating the degradation products of the glycoprotein from step (a) by size exclusion chromatography; and (c) analyzing fractions from step (b) containing said degradation products by mass spectrometry, wherein the molecular masses of the degradation products are indicative of the boundaries of the degradation products, and thus indicative of amino acid residues (e.g., those at the boundaries of the degradation products) in glycoproteins that render the glycoproteins susceptible to degradation.

Further, the present invention provides methods for screening a modified IgG for increased stability, said method comprising:(a) heating at 55° C. for a week a modified IgG having one or more amino acid modifications in the hinge region of said IgG at a position corresponding to from position 233 to position 239 of human IgG1 and/or an amino acid modification at a position corresponding to position 249 of human IgG1; (b) fractionating the degradation products of the modified IgG from step (a) by size exclusion chromatography; and (c) analyzing fractions from step (b) containing said degradation products by mass spectrometry, wherein the production of fewer degradation products by said modified IgG as compared to an IgG not having said one or more amino acid modifications indicates that said modified IgG has increased stability.

In the foregoing methods of identifying amino acid residues in glycoproteins that render the glycoproteins susceptible to degradation and of screening for a modified immunoglobulin with increased stability, the glycoprotein/modified IgG or degradation products can be chemically or enzymatically modified prior to their analysis by mass spectrometry, for example by desalting, reduction, alkylation and/or deglycosylation. Further, any type of mass spectrometry can be used for this analysis, for example, Matrix Assisted Laser Desorption Ionization-Time of Flight Mass Spectrometry (MALDI-TOF-MS) or Liquid Chromatography Electrospray Ionization Mass Spectrometry (LC-ESI-MS).

Included within the invention are pharmaceutical compositions and methods of prophylaxis and therapy using stabilized immunoglobulins or other bioactive molecules of the invention having extended storage stability and/or in vivo half-life. The present invention provides pharmaceutical compositions comprising the stabilized glycoproteins, most preferably the stabilized immunoglobulins, of the present invention. In a specific embodiment, the pharmaceutical compositions are formulated into a liquid formulation. In certain embodiments, the pharmaceutical compositions are formulated for parenteral, subcutaneous, intravenous, intramuscular, intranasal, or pulmonary delivery. The pharmaceutical compositions of the present invention are preferably exhibit long term-stability. In a certain specific embodiment, the pharmaceutical compositions are stable at ambient temperature for at least 1 year, as determined by HPSEC. In another specific embodiment, the pharmaceutical compositions are stable at 40° C. for at least 100 days as determined by HPSEC. In yet another specific embodiment, the pharmaceutical compositions are stable at 4° C. for at least 3 years, for 3-5 years, or for at least 5 years as determined by HPSEC.

Also provided by the present invention are methods of diagnosis using stabilized glycoproteins, such as immunoglobulins, proteins and other bioactive molecules. In a specific embodiment, the invention provides a stabilized anti-respiratory syncytial virus (RSV) antibody useful to treat or prevent RSV infection, such as a stabilized form of SYNAGIS® (palivizumab) (see U.S. Pat. No. 5,824,307 and Johnson et al., J. Infectious Disease 176:1215-1224, 1997, both of which are incorporated by reference in their entireties), and other anti-RSV antibodies, including variants of SYNAGIS® (see U.S. patent application Ser. No. 09/724,396, filed Nov. 28, 2000, U.S. patent application Ser. No. 09/724,53 1, filed Nov. 28, 2000, U.S. patent application Ser. No. 09/996,288 filed Nov. 28, 2001, and U.S. patent application Ser. No. 09/996,265 filed Nov. 28, 2001, all entitled "Methods of Administering/Dosing Anti-RSV Antibodies for Prophylaxis and Treatment," all by Young et al., all of which are incorporated by reference herein in their entireties, particularly the sequences of heavy and light chain variable domains and CDRs of anti-RSV antibodies disclosed therein). In a preferred embodiment, a stabilized anti-RSV antibody has one or more amino acid modifications in the heavy chain constant domain hinge region that renders the antibody less susceptible to degradation.

3.1. Definitions

The term "immunoglobulin heavy chain hinge region", "heavy chain hinge region" as used herein refers to a region of an immunoglobulin molecule consisting of the hinge region, located between the CH1 and CH2 domains.

The term "immunoglobulin heavy chain upper hinge region" or "heavy chain upper hinge region" refers to the amino terminal portion of an immunoglobulin heavy chain hinge region. In human IgG1 immunoglobulins, the heavy chain upper hinge region spans amino acid glutamic acid 226 and proline 243. The amino acid sequence of human IgG1 upper heavy chain hinge region and other exemplary hinge regions is provided in Table 5, infra. Amino acid numbering is given according to the Kabat numbering scheme (Kabat, E. A., T. T. Wu, H. M. Perry, K. S. Gottesman, and Foeller. 1991. Sequences of Proteins of Immunological Interest, U.S. Public Health Service, National Institutes of Health, Washington, D.C.), unless otherwise indicated.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

A "stabilizing mutation" or "stabilizing modification" is one in which a destabilizing amino acid, for example a labile amino acid (e.g., histidine or threonine) or reactive amino acid (e.g., lysine or glutamic acid) is deleted or substituted, for example, with a bulky inactive amino acid (e.g., valine or isoleucine), which mutation or modification results in reduced degradation of a protein comprising the mutation or modification relative to non-mutated or unmodified counterpart. A "stabilizing point mutation" is one where a destabilizing amino acid, for example a labile or reactive amino acid, is substituted with another amino acid, which substitution results in reduced degradation of a protein comprising the substation relative to a counterpart without the substitution. One exemplary stabilizing point mutation is the substitution of serine 241 with proline in human IgG4 heavy chain hinge region.

The terms "stabilized" and "stable" as used herein in the context of a glycoprotein, including but not limited to an antibody or immunoglobulin, with a stabilizing mutation or modification, resulting in increased storage stability and/or in vivo half life. An exemplary stabilized human immunoglobulin is one of the IgG4 class in which is serine 241 in the heavy chain hinge region is substituted with proline.

When referring to a stabilized glycoprotein with increased storage stability, the terms "stabilized" and "stable" refer to reduced levels of degradation under storage conditions relative to the corresponding glycoprotein without the stabilizing mutation or modification. The "stabilized" and "stable" glycoproteins of the invention exhibit at least a 10% reduction in degradation relative to the corresponding glycoprotein without the stabilizing mutation. In certain embodiments, the stabilized and stable glycoproteins of the invention exhibit at least a 20%, 30%, 40%, 50%, 60%, 70%, 80%, 90% or 95% reduction in degradation relative to the corresponding glycoprotein without the stabilizing mutation. The stability of a stabilized or stable glycoprotein with increased storage stability can be assessed by degrees of aggregation, degradation or fragmentation by methods known to those skilled in the art, including but not limited to reduced Capillary Gel Electrophoresis (rCGE), Sodium Dodecyl Sulfate Polyacrylamide Gel Electrophoresis (SDS-PAGE) and high performance size exclusion chromatography (HPSEC), compared to the corresponding glycoprotein without the stabilizing mutation or modification. In a preferred embodiment, the percentage reduction in degradation in a stabilized glycoprotein with increased storage stability is represented by the percentage reduction in one or more degradation products following exposure to heat, e.g., upon heating the glycoprotein at 55° C. for a one-week period, relative to the amount of degradation product in the corresponding glycoprotein without the stabilizing mutation or modifications under the same conditions. Alternatively, storage stability may be manifested as percentage reduction in one or more degradation products following long-term (i.e., three months, six months, or one, two or three or more years) storage at ambient temperature and/or 4° C., relative to the amount of degradation product in the corresponding glycoprotein without the stabilizing mutation or modifications under the same conditions.

When referring to a stabilized glycoprotein with increased in vivo half-life, the terms "stabilized" and "stable" refer to a glycoprotein with a stabilizing mutation that increases the molecule's biological half-life in the circulation of a given animal and is represented by a time required for half the quantity administered in the animal to be cleared from the circulation and/or other tissues in the animal. When a clearance curve of a given glycoprotein is constructed as a function of time, the curve is usually biphasic with a rapid $\alpha$-phase which represents an equilibration of the injected glycoproteins between the intra- and extra-vascular space and which is, in part, determined by the size of molecules, and a longer $\beta$-phase which represents the catabolism of the glycoproteins in the intravascular space. The term "in vivo half-life" practically corresponds to the half life of the glycoproteins in the $\beta$-phase. The "stabilized" and "stable" glycoproteins of the invention with increased half-lives exhibit at least a 10% increase in in vivo half-life relative to the corresponding glycoprotein without the stabilizing mutation. In certain embodiments, the stabilized" and "stable" glycoproteins of the invention with increased in vivo half-lives exhibit at least a 20%, 30%, 40%, 50%, 60%, 70%, 80%, 90% or 95% increase in in vivo half-life relative to the corresponding glycoprotein without the stabilizing mutation.

"Degradation", as used herein and unless otherwise indicated, is independent of mechanism and refers to any chemical or biological fragmentation of a protein, more specifically a glycoprotein (e.g., immunoglobulin or antibody), for example by hydrolysis or proteolytic cleavage.

An "isolated" or "purified" stabilized glycoprotein (e.g., immunoglobulin or antibody, as well as a fusion protein comprising a stabilized glycoprotein) is substantially free of cellular material or other contaminating proteins from the cell or tissue source from which the protein is derived, or substantially free of chemical precursors or other chemicals when chemically synthesized. The language "substantially free of cellular material" includes preparations of a stabilized glycoprotein in which the stabilized glycoprotein is separated from cellular components of the cells from which it is isolated or recombinantly produced. Thus, a stabilized glycoprotein that is substantially free of cellular material includes preparations of stabilized glycoprotein having less than about 30%, 20%, 10%, or 5% (by dry weight) of contaminating protein. When the a stabilized glycoprotein is recombinantly produced, it is also preferably substantially free of culture medium, i.e., culture medium represents less than about 20%, 10%, or 5% of the volume of the protein preparation. When the stabilized glycoprotein is produced by chemical synthesis, it is preferably substantially free of chemical precursors or other chemicals, i.e., it is separated from chemical precursors or other chemicals which are involved in the synthesis of the protein. Accordingly such preparations of the stabilized glycoprotein have less than about 30%, 20%, 10%, 5% (by dry weight) of chemical precursors or compounds other than the stabilized glycoprotein. In a preferred embodiment of the present invention, stabilized glycoproteins are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. An "isolated" nucleic acid molecule does not include cDNA molecules within a cDNA library. In a preferred embodiment of the invention, nucleic acid molecules encoding antibodies are isolated or purified. In another preferred embodiment of the invention, nucleic acid molecules encoding stabilized glycoproteins are isolated or purified.

The term "host cell" as used herein refers to the particular subject cell transfected with a nucleic acid molecule or infected with phagemid or bacteriophage and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

Where the names of amino acids are abbreviated, the names are abbreviated either with three-letter or one-letter symbols.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, *Proc. Natl. Acad. Sci. U.S.A.* 87:2264-2268, modified as in Karlin and Altschul, 1993, *Proc. Natl. Acad. Sci. U.S.A.* 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, *Nucleic Acids Res.* 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used. Another preferred, non-limiting example of a mathematical algorithm utilized for the comparison of sequences is the algorithm of Myers and Miller, 1988, *CABIOS* 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

4. DESCRIPTION OF THE FIGURES AND TABLES

FIG. 1: Size exclusion chromatography (SEC) of heat-stressed MAb A.

FIG. 2: MALDI-TOF-MS mass spectra of A) non-deglycosylated and B) deglycosylated SEC fraction 'Peak 1' of the heat-stressed MAb A.

FIGS. 3A and 3B: MALDI-TOF-MS mass spectra of A) non-deglycosylated and reduced and B) deglycosylated and reduced SEC fraction 'Peak 1' of the heat-stressed MAb A.

FIG. 4: MALDI-TOF-MS mass spectra of A) non-deglycosylated and B) deglycosylated SEC fraction 'Peak 2' of the heat-stressed MAb A.

FIGS. 5A and 5B: MALDI-TOF-MS mass spectra of A) non-deglycosylated and reduced and B) deglycosylated and reduced SEC fraction 'Peak 2' of the heat-stressed MAb A.

FIGS. 6A-6C: RP-HPLC chromatography for LC-ESI-MS analysis of deglycosylated, reduced, and alkylated: A) SEC fraction 'Peak 1', B) SEC fraction 'Peak 2', and C) non-heated reference standard of MAb A.

FIGS. 7A-7D: Reconstructed ESI-MS mass spectra for each peak A) 1-B, B) 1-C, C) 1-D, and D) 1-E shown in RP-HPLC chromatogram of deglycosylated, reduced, and alkylated SEC fraction 'Peak 1' of MAb A (FIG. 6A).

FIG. 8: Expansion of the reconstructed mass spectrum shown in FIG. 7A.

FIGS. 9A-9C: Reconstructed ESI-MS mass spectra for each peak A) 2-B, B) 2-C, and C) 2-D, shown in RP-HPLC chromatogram of deglycosylated, reduced, and alkylated SEC fraction 'Peak 2' of MAb A (FIG. 6B).

FIG. 10: Expansion of the reconstructed mass spectra shown in FIG. 9.

FIG. 11: Experimental scheme for identification and analysis of immunoglobulin degradation sites and products.

Figure 12:
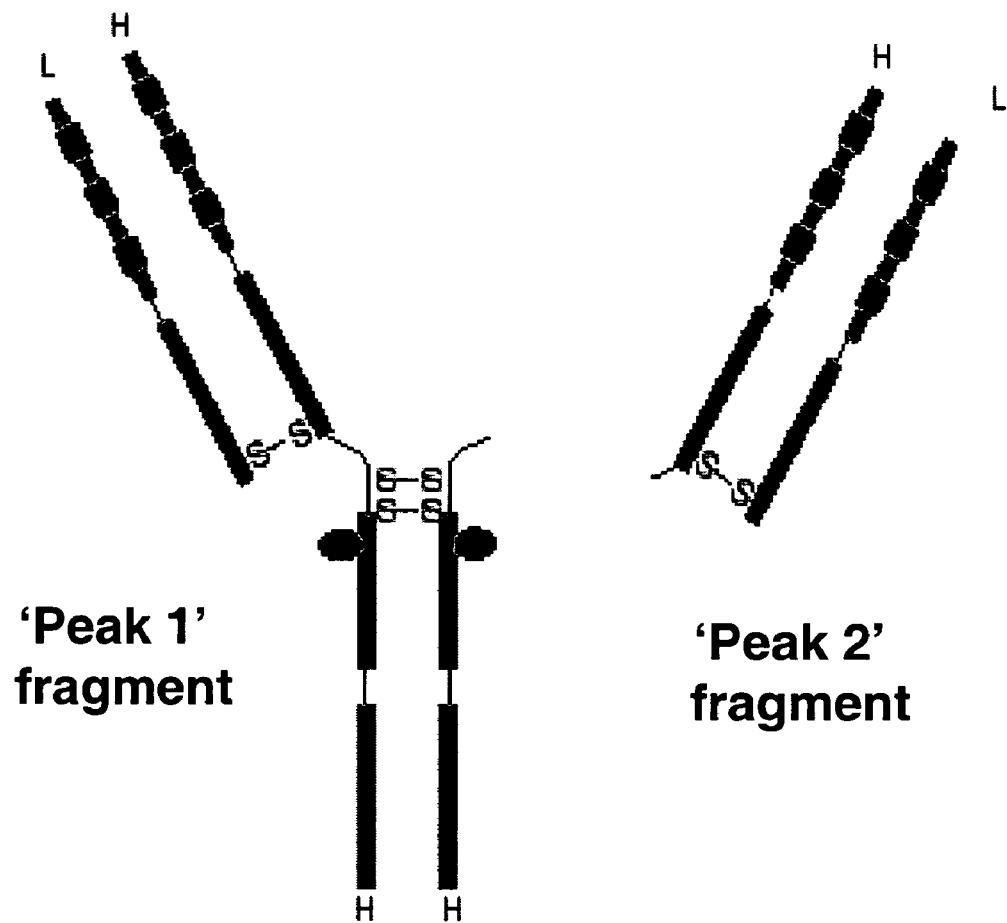

FIG. 12: Heat-induced fragmentation of MAbs.

Table 1: Molecular weight of analysis of the SEC fraction 'Peak 1' of heat-stressed MAb A with MALDI-TOF-MS.

Table 2: Molecular weight of analysis of the SEC fraction 'Peak 2' of heat-stressed MAb A with MALDI-TOF-MS.

Table 3: Components identified in the deglycosylated, reduced, and alkylated SEC fraction 'Peak 1' of heat-stressed MAb A with LC-ESI-MS. The amino acid positions referred to in Table 3 correspond to amino acid positions along the sequence of the anti-CD2 antibody Medi-507 (PCT Publication No. WO 99/03502). Amino acids 221-227 of Medi-507 correspond to Kabat positions 233-239.

Table 4: Components identified in the deglycosylated, reduced, and alkylated SEC fraction 'Peak 2' of heat-stressed MAb A with LC-ESI-MS. The amino acid positions referred to in Table 4 correspond to amino acid positions along the sequence of the anti-CD2 antibody Medi-507 (PCT Publication No. WO 99/03502). Amino acids 221-227 of Medi-507 correspond to Kabat positions 233-239.

5. DETAILED DESCRIPTION OF THE INVENTION

The present invention relates to molecules, particularly proteins, more particularly glycoproteins, and yet more particularly immunoglobulins, with stabilizing modifications. Such molecules are referred to herein as "stabilized". Stabilized molecules of the invention have an increased storage stability and/or increased in vivo half-life when administered to a patient or subject. The stabilized molecules of the invention contain one or more amino acid modifications relative to their unmodified (or "non-stabilized" counterparts), which modifications result in removal or substitution of an amino acid, for example a labile or reactive amino acid, that is detrimental to the stability of the molecule. In a preferred embodiment, the invention particularly relates to the modification of glycoproteins which have particular use in human therapy, prophylaxis and diagnosis. In certain preferred embodiments, the glycoproteins are immunoglobulins, preferably human or humanized IgGs and other non-IgG immunoglobulins, that are modified at the CH2 region, for example at the amino acid corresponding in human IgG1 to Kabat position 249, or, more preferably, at the heavy chain hinge region, most preferably at amino acids corresponding to one, a combination or all the amino acids at the upper hinge region, corresponding in human IgG1 to Kabat positions 226-243.

5.1. Methods of Identifying Regions of Immunoglobulin Molecules Susceptible to Degradation The present invention relates to a method for characterizing degradation products of a glycoprotein. In general, a solution of the glycoprotein is exposed to a temperature of about 55° C. for about one week. The solution is subsequently fractionated by size-exclusion chromatography. Glycoprotein or glycoprotein degradation product containing fractions eluted from the size-exclusion column are optionally purified, desalted, chemically modified or enzymatically modified and subjected to mass spectrometry analysis. Examples of chemical modification included, but are not limited to, desalting, reduction, alkylation or deglycosylation. An example of enzymatic modification includes, but is not limited to, deglycosylation. The glycoprotein or glycoprotein degradation products can optionally undergo an additional chromatographic step after chemical or enzymatic modification but prior to mass spectrometry analysis.

The glycoprotein or glycoprotein degradation products which have been optionally chemically or enzymatically modified are then characterized using mass spectrometry. Mass spectrometry techniques particularly useful in the present invention include, but are not limited to, Matrix Assisted Laser Desorption Ionization-Time Of Flight Mass Spectrometry ("MALDI-TOF-MS") and Liquid Chromatography Electrospray Ionization Mass Spectrometry ("LC-ESI-MS"). The resulting mass spectra can then be used to determine the identity of the degradation products.

In one embodiment, the present invention relates to a method for characterizing degradation products of a glycoprotein comprising mass spectrometry analysis of a composition comprising glycoprotein degradation products.

In one embodiment, the glycoprotein is an antibody. In another embodiment, the glycoprotein is a monoclonal antibody.

In one embodiment, the glycoprotein has been exposed to a temperature above room temperature prior to mass spectrometry analysis. In a particular embodiment, the temperature is about 40° C. to about 50° C., about 50° C. to about 60° C., about 60° C. to about 70° C. or about 70° C. to about 80° C. In a preferred embodiment, the temperature is about 55° C.

In one embodiment, the glycoprotein has been exposed to acidic conditions prior to mass spectrometry analysis. In a particular embodiment, the pH is about 6.5 to about 5.5, about 5.5 to about 4.5, about 4.5 to about 3.5, about 3.5 to about 2.5, about 2.5 to about 1.5, or less then 1.5.

In one embodiment, the glycoprotein has been exposed to basic conditions prior to mass spectrometry analysis. In a particular embodiment, the pH is about 7.5 to about 8.5, about 8.5 to about 9.5, about 9.5 to about 10.5, about 10.5 to about 11.5, about 11.5 to about 12.5, or greater then 12.5.

In one embodiment, the glycoprotein degradation products are chromatographically separated prior to mass spectrometry analysis. In a particular embodiment, the glycoprotein degradation products are separated using size-exclusion chromatography prior to mass spectrometry analysis. In another embodiment, the glycoprotein degradation products are separated using affinity chromatography prior to mass spectrometry analysis. In another embodiment, the glycoprotein degradation products are separated using ion-exchange chromatography prior to mass spectrometry analysis.

In one embodiment, the glycoprotein degradation products are desalted prior to mass spectrometry analysis.

In one embodiment, the glycoprotein degradation products are chemically modified prior to mass spectrometry analysis. In a particular embodiment, the glycoprotein degradation products are chemically reduced reduction prior to mass spectrometry analysis. In another embodiment, the glycoprotein degradation products are alkylated prior to mass spectrometry analysis. In another embodiment, the glycoprotein degradation products are chemically reduced and alkylated prior to mass spectrometry analysis. In another embodiment, the glycoprotein degradation products are chemically deglycosylated prior to mass spectrometry analysis.

In one embodiment, the glycoprotein degradation products are enzymatically modified prior to mass spectrometry analysis. In a particular embodiment, the glycoprotein degradation products are enzymatically deglycosylated prior to mass spectrometry analysis.

In one embodiment, the mass spectrometry analysis further comprises a chromatographic step.

In one embodiment, the mass spectrometry analysis is Matrix Assisted Laser Desorption Ionization-Time Of Flight Mass Spectrometry ("MALDI-TOF-MS").

In one embodiment, the mass spectrometry analysis is Liquid Chromatography Electrospray Ionization Mass Spectrometry ("LC-ESI-MS").

The mass spectrometric methods of identifying glycoprotein degradation products are useful where the degradation product is present in small amounts. However, any other method of determining protein or peptide sequences known to one of skill in the art to identify glycoprotein degradation products. For example, if present in sufficient quantities, a degradation product can be gel purified and subjected to microsequencing to identify precisely the boundaries of the degradation product.

5.2. Methods of Measuring Glycoprotein Stability

There are various methods available for assessing the storage stability of the modified glycoproteins of the invention, based on the physical and chemical structures of the proteins as well as on their biological activities. For example, to study denaturation of proteins, methods such as charge-transfer absorption, thermal analysis, fluorescence spectroscopy, circular dichroism, NMR, rCGE, SDS-PAGE, and HPSEC, are available. See, for example, Wang et al., 1988, *J. of Parenteral Science & Technology* 42(Suppl):S4-S26.

Among these methods, rCGE, SDS-PAGE and HPSEC are the most common and simplest methods to assess not only denaturation of proteins based on detection of protein aggregates but also protein degradation and fragmentation. Accordingly, the stability of the modified glycoproteins of the present invention may be assessed by these methods.

For example, the stability of the modified glycoproteins of the present invention may be evaluated by the % area of the peaks representing the non-degraded non-modified counterpart of the glycoprotein in HPSEC or rCGE, or % density of protein bands representing the same in SDS-PAGE.

In other embodiments, the stability of the modified glycoproteins is evaluated as a reduction in the % area of the peaks representing one or more degradation products in the modified glycoprotein relative to the area of the corresponding peaks in the unmodified counterparts. For example, in certain embodiments, the area of the peaks representing one or more degradation products in the modified glycoprotein is 10%, 20%, 30%, 40%, 50%, 60%, 70%, 80%, 90% or 95% that the corresponding peak in an unmodified counterpart subjected to the same conditions.

The stabilized glycoproteins of the present invention preferably exhibit low to undetectable levels of aggregation as measured by HPSEC or rCGE. In preferred embodiments, the stabilized glycoproteins of the invention exhibit no more than 5%, no more than 4%, no more than 3%, no more than 2%, no more than 1%, and most preferably no more than 0.5% aggregate by weight protein, and/or low to undetectable levels of fragmentation, that is, 80% or higher, 85% or higher, 90% or higher, 95% or higher, 98% or higher, or 99% or higher, or 99.5% or higher of the total peak area in the peak(s) representing the intact stabilized glycoprotein. In the case of SDS-PAGE, the density or the radioactivity of each band stained or labeled with radioisotope can be measured and the % density or % radioactivity of the band representing degraded and/or non-degraded glycoprotein (both modified and unmodified) can be obtained.

The stability of the modified glycoproteins of the present invention can be also assessed by any assays which measures their biological activity. For modified glycoproteins that are antibodies, the biological activity of an antibody includes, but not limited to, antigen-binding activity, complement-activation activity, Fc-receptor binding activity, and so forth. Antigen-binding activity of an antibody can be measured by any method known to those skilled in the art, including but not limited to ELISA, radioimmunoassay, Western blot, and the like. Complement-activation activity can be measured by a C3a/C4a assay in the system where the stabilized antibody is reacted in the presence of the complement components with the cells expressing the antigen to which the antibody immunospecifically binds. Also see Harlow et al., Antibodies: A Laboratory Manual, (Cold Spring Harbor Laboratory Press, 2nd ed. 1988) (incorporated by reference herein in its entirety).

5.3. Identification of Stabilizing Mutations Within the Hinge-FC Region of Immunoglobulin Molecules Methods of identifying and/or incorporating one or more stabilizing mutations render a glycoprotein, including but not limited to an antibody or immunoglobulin, less susceptible in degradation are encompassed by the methods of the present invention. In a preferred embodiment, such stabilizing modification are made in IgG residues 226-243, more preferably in IgG residue histidine 237, or corresponding residues of other immunoglobulin molecules. These modifications may be introduced utilizing any technique known to those of skill in the art.

A glycoprotein stabilizing modification, for example a stabilizing modification in the heavy chain hinge region at amino acid residues 226-243 or a stabilizing modification in the heavy chain CH1 domain at amino acid residue 249, may be screened by, for example, by assaying glycoprotein stability according to the methods described herein (e.g., as described in Section 5.1 or 5.2, supra). Those modifications in therapeutic glycoproteins, e.g., in the heavy chain hinge region which increase the stability of the immunoglobulin can be introduced into to increase the storage stability or in vivo half-lives of said glycoproteins.

In certain embodiments, incorporating a stabilizing point mutation into a glycoprotein can entail substituting a non-polar amino acid (alanine, valine, leucine, isoleucine, proline, phenylalanine, tryptophan or methionine) with another non-polar amino acid, a polar but uncharged amino acid (glycine, serine, cystine, asparagine, glutamine, tyrosine or threonine), a polar amino acid that is positively charged (lysine, arginine, histidine), or a polar amino acid that is negatively charged (aspartic acid, glutamine acid).

In other embodiments, incorporating a stabilizing point mutation into a glycoprotein can entail substituting a polar but uncharged amino acid with another polar but uncharged amino acid, with a non-polar amino acid, with a polar amino acid that is positively charged, or with a polar amino acid that is negatively charged.

In yet other embodiments, incorporating a stabilizing point mutation into a glycoprotein can entail substituting a polar amino acid that is positively charged with another polar amino acid that is positively charged, with a non-polar amino acid, with a polar but uncharged amino acid, or with a polar amino acid that is negatively charged.

In yet other embodiments, incorporating a stabilizing point mutation into a glycoprotein can entail substituting a polar amino acid that is negatively charged with another polar amino acid that is negatively charged, with a non-polar amino acid, with a polar but uncharged amino acid, or with a polar amino acid that is positively charged.

In a specific embodiment, incorporating a stabilizing point mutation into a glycoprotein can entail substitution of a proline residue with a non-proline residue.

In another specific embodiment, incorporating a stabilizing point mutation into a glycoprotein can entail substitution of a histidine, threonine, lysine or glutamic acid with a valine or isoleucine.

5.3.1. Mutagenesis

Mutagenesis may be performed in accordance with any of the techniques known in the art including, but not limited to, synthesizing an oligonucleotide having one or more modifications within the sequence of the heavy chain hinge region of an immunoglobulin to be modified. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered. A number of such primers introducing a variety of different mutations at one or more positions may be used to generated a library of mutants.

The technique of site-specific mutagenesis is well known in the art, as exemplified by various publications (see, e.g.,. Kunkel et al., *Methods Enzymol.*, 154:367-82, 1987, which is hereby incorporated by reference in its entirety). In general, site-directed mutagenesis is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as T7 DNA polymerase, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as E. coli cells, and clones are selected which include recombinant vectors bearing the mutated sequence arrangement. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

Alternatively, the use of PCR™ with commercially available thermostable enzymes such as Taq DNA polymerase may be used to incorporate a mutagenic oligonucleotide primer into an amplified DNA fragment that can then be cloned into an appropriate cloning or expression vector. See, e.g., Tomic et al., *Nucleic Acids Res.*, 18(6):1656, 1987, and Upender et al., *Biotechniques*, 18(1):29-30, 32, 1995, for PCR™-mediated mutagenesis procedures, which are hereby incorporated in their entireties. PCR™ employing a thermostable ligase in addition to a thermostable polymerase may also be used to incorporate a phosphorylated mutagenic oligonucleotide into an amplified DNA fragment that may then be cloned into an appropriate cloning or expression vector (see e.g., Michael, *Biotechniques*, 16(3):410-2, 1994, which is hereby incorporated by reference in its entirety).

Other methods known to those of skill in art of producing stabilizing modifications of a glycoprotein of interest can be used. For example, recombinant vectors encoding the amino acid sequence of the heavy chain constant domain of an antibody or a fragment thereof may be treated with mutagenic agents, such as hydroxylamine, to obtain sequence variants.

5.3.2. Sequencing

Any of a variety of sequencing reactions known in the art can be used to directly sequence the nucleotide sequence encoding a glycoprotein with a stabilizing modification, for example an immunoglobulin with a stabilizing modification in a heavy chain hinge region. Examples of sequencing reactions include those based on techniques developed by Maxim and Gilbert (*Proc. Natl. Acad. Sci. USA*, 74:560, 1977) or Sanger (*Proc. Natl. Acad. Sci. USA*, 74:5463, 1977). It is also contemplated that any of a variety of automated sequencing procedures can be utilized (*Bio/Techniques*, 19:448, 1995), including sequencing by mass spectrometry (see, e.g., PCT Publication No. WO 94/16101, Cohen et al., *Adv. Chromatogr.*, 36:127-162, 1996, and Griffin et al., *Appl. Biochem. Biotechnol.*, 38:147-159, 1993).

5.4. Stabilized Immunoglobulin Molecules

The present invention is based in part upon the identification of immunoglobulin heavy chain hinge regions as being susceptible to degradation, for example through hydrolysis upon heating. The present invention thus provides stabilized immunoglobulin molecules with amino acid modifications at the heavy chain hinge regions and/or in CH2 domains that render the immunoglobulin molecules less susceptible to degradation. Such stabilized immunoglobulin molecules comprise one or more mutations in the heavy chain hinge regions and/or one or more mutations in CH2 domains. In preferred embodiments, the one or more amino acid modifications are made in one or more of heavy chain hinge region residues, most preferably in upper hinge region residues (corresponding to Kabat amino acid 226-243 in human IgG1 or analogous residues thereof) The sequences of heavy chain hinge regions and flanking amino acids are commonly known to the skilled artisan. Exemplary heavy chain hinge region sequences (utilizing the Kabat numbering system; Kabat et al., 1991, Sequences of Proteins of Immunological Interest, U.S. Public Health Service, National Institutes of Health, Washington, D.C.) are provided in Table 5 below:

TABLE 5

Upper heavy chain hinge region sequences from exemplary immunoglobulin molecules. Where available, the number of each amino acid according to the Kabat numbering scheme is provided in parentheses following the amino acid.

| Organism/ Immunoglobulin | Upper heavy chain hinge region sequence |
| --- | --- |
| Human gamma 1 | E(226)P(227)K(228)S(232)C(233)D(234)K(235)T(236) H(237)T(238)C(239)P(240)P(241)C(242)P(243) |
| Human gamma 2 | E(226)R(227)K(228)C(232)C(233)V(235)E(237)C(239)P(240) P(241)C(242)P(243) |
| Human gamma 3 (exon 1) | E(226)L(227)K(228)T(229)P(230)L(232)G(233)D(234)T(235) T(236)H(237)T(238)C(239)P(240)R(241)C(241A)P(241B)E(241C) P(241D)K(241E)S(241F)C(241G)D(241H)T(241I)P(241J)P(241K) P(241L)C(241M)P(241N)R(241O)C(241P)P(241Q)E(241R)P(241S) K(241T)S(241U)C(241V)D(241W)T(241X)P(241Y)P(241Z)P(241AA) C(241BB)P(241CC)R(241DD)C(241EE)P(241FF)E(241GG)P(241HH) K(241II)S(241JJ)C(241KK)D(241LL)T(241MM)P(241NN)P(241OO) P(241PP)C(241QQ)P(241RR)R(241SS)C(242)P(243) |
| Human gamma 3 (exon 2, 3 and 4) | E(226)P(227)K(228)S(232)C(233)D(234)T(235)P(236)P(237) P(238)C(239)P(240)R(241)C(242)P(243) |
| Human gamma 4 | E(226)S(227)K(228)Y(229)G(230)P(237)P(238)C(239)P(240) S(241)C(242)P(243) |
| Mouse gamma 2a | E(226)P(227)R(228)G(229)P(230)T(231)I(232)K(235)P(236) C(237)P(238)P(239)C(240)K(241)C(242)P(243) |
| Mouse gamma 1 | V(226)P(227)R(228)D(229)C(235)G(236)C(237)K(238)P(239) C(240)I(241)C(242)T(243) |

TABLE 5-continued

Upper heavy chain hinge region sequences from exemplary immunoglobulin molecules. Where available, the number of each amino acid according to the Kabat numbering scheme is provided in parentheses following the amino acid.

| Organism/ Immunoglobulin | Upper heavy chain hinge region sequence |
| --- | --- |
| Rat gamma 1 | V(226)P(227)R(228)N(229)C(233)G(234)G(235)D(236)C(237)K(238)P(239)C(240)I(241)C(242)T(243) |
| Rat gamma 2a | V(229)P(230)R(231)E(236)C(237)N(238)P(239)C(240)G(241)C(242)T(243) |
| Rat gamma 2c | E(229)P(230)R(231)R(232)P(233)K(234)P(235)R(236)P(237)P(238)T(239)D(240)I(241)C(241A)S(241B)C(241C) |
| Sheep gamma 1 | E(226)P(227)G(229)C(230)P(232)D(235)P(236)C(237)K(238)H(239)C(240)R(241)C(242)P(243) |
| Dog gamma | FNECRCTDTPPCPVPEP |

In certain preferred embodiments, the stabilized immunoglobulin molecules of the invention have one or a combination of more than one of the stabilizing point mutations listed in Table 6 below:

TABLE 6

Exemplary heavy chain hinge region stabilizing mutations.

| Heavy chain hinge region position | Stabilizing point mutation(s) |
| --- | --- |
| Cysteine 233 and/or cysteine 239 (human gamma 1) | Alanine, arginine, asparagine, aspartic acid, glutamic acid, glutamine, glycine, histidine, isoleucine, leucine, lysine, methionine, phenylalanine, proline, serine, threonine, tryptophan, tyrosine, or valine |
| Aspartic Acid 234 (human gamma 1) | Alanine, arginine, asparagine, cysteine, glutamic acid, glutamine, glycine, histidine, isoleucine, leucine, lysine, methionine, phenylalanine, proline, serine, threonine, tryptophan, tyrosine, valine |
| Lysine 235 (human gamma 1) | Alanine, arginine, asparagine, aspartic acid, cysteine, glutamic acid, glutamine, glycine, histidine, isoleucine, leucine, methionine, phenylalanine, proline, serine, threonine, tryptophan, tyrosine, valine |
| Threonine 236 and/or threonine 239 (human gamma 1) | Alanine, arginine, asparagine, aspartic acid, cysteine, glutamic acid, glutamine, glycine, histidine, isoleucine, leucine, lysine, methionine, phenylalanine, proline, serine, tryptophan, tyrosine, valine |
| Histidine 237 (human gamma 1) | Alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine |
| Serine 236 (human gamma 4) | Proline |

In a preferred embodiment, the stabilizing modifications do not abolish, or, more preferably, do not alter, other immune effector or receptor binding functions of the constant domain, for example, but not limited to complement fixation, ADCC and binding to FcγRI, FcγRII, and FcγRIII, as can be determined by methods well-known and routine in the art. In another preferred embodiment, the modified hinge region of the constant domain does not contain sequences that mediate immune effector functions or other receptor binding. In yet another embodiment, the effector functions are selectively altered (e.g., to reduce or increase effector functions).

In a specific embodiment, the heavy chain or upper heavy chain hinge region has a substitution at 1, 2, 3, 4, 5, 6, 7, 8, 9, 10, 12, 13, 14, 15 or more of residues. In another specific embodiment, the heavy chain or upper heavy chain hinge region has substitutions at all its residues. In an exemplary embodiment, the IgG1 heavy chain hinge region has a substitution at 1, 2, 3, 4, 5, 6, 7, 8, 9, 10, 12, 13, 14, or all 15 of residues 226-243.

The stabilized immunoglobulins of the invention may comprise, in addition or in place of one or more modifications at the heavy chain hinge regions, one or more modifications in sequences flanking the heavy chain hinge regions, for example the CH1 or CH2 domains. For example, stabilized immunoglobulin of the present invention can have one or more stabilizing mutations in the CH2 domain immediately C terminal to the hinge region. In a preferred embodiment, the stabilized immunoglobulin has one or more stabilizing mutations in one or more of the following amino acids: L(247)L(248)G(249)G(250)P(251) of human IgG1 or corresponding residues in other immunoglobulins. In a specific preferred embodiment, the mutation is at IgG1 position 249. In a specific embodiment, the glycine at position 249 of IgG1 is substituted with alanine, arginine, asparagine, aspartic acid, cysteine, glutamic acid, glutamine, histidine, isoleucine, leucine, lysine, methionine, phenylalanine, proline, serine, threonine, tryptophan, tyrosine, or valine.

Amino acid modifications can be made by any method known in the art and many such methods are well known and routine for the skilled artisan. For example, but not by way of limitation, amino acid substitutions, deletions and insertions may be accomplished using any well-known PCR-based technique. Amino acid substitutions may be made by site-directed mutagenesis (see, for example, Zoller and Smith, *Nucl. Acids Res.* 10:6487-6500, 1982; Kunkel, *Proc. Natl. Acad. Sci USA* 82:488, 1985, which are hereby incorporated by reference in their entireties). Mutants that result in increased stability may readily be screened using well-known and routine assays, such as those described in Section 5.11, infra. In a preferred method, amino acid substitutions are introduced at one or more residues in the heavy chain constant domain hinge region and the mutated constant domains or fragments are expressed on the surface of bacteriophage which are then screened for increased stability (see, in particular, Section 5.2 and 5.11, infra).

In one preferred embodiment, the invention provides stabilized immunoglobulin molecules (e.g., various antibodies) that have increased storage stability and/or in vivo half-life relative to unmodified molecules (and, in preferred embodiments, altered bioavailabilty such as increased or decreased transport to mucosal surfaces or other target tissues). Such immunoglobulin molecules include IgG of any subtype (IgG1, IgG2, IgG3, IgG4, and IgG5) and other non-IgG immunoglobulins (e.g., IgE, IgM, IgD, IgA and IgY).

The stabilized immunoglobulins include any immunoglobulin molecule that binds (preferably, immunospecifically, i.e., competes off non-specific binding), as determined by immunoassays well known in the art for assaying specific antigen-antibody binding) an antigen. Such antibodies include, but are not limited to, polyclonal, monoclonal, bi-specific, multi-specific, human, humanized, or chimeric antibodies that specifically bind an antigen.

The stabilized IgG molecules of the invention, are preferably IgG1 subclass of IgGs, but may also be any other IgG subclasses of given animals. For example, in humans, the IgG class includes IgG1, IgG2, IgG3, and IgG4; and mouse IgG includes IgG1, IgG2a, IgG2b, IgG2c and IgG3. It is known that certain IgG subclasses, for example, mouse IgG2b and IgG2c, have higher clearance rates than, for example, IgG1 (Medesan et al., *Eur. J. Immunol.,* 28:2092-2100, 1998). Thus, when using IgG subclasses other than IgG1, it may be advantageous to substitute one or more of the residues, particularly in the CH2 (other than a stabilizing point mutation in a CH2 domain) and CH3 domains, that differ from the IgG1 sequence with those of IgG1, thereby increasing storage stability and/or in vivo half-lives of the other types of IgG.

The stabilized immunoglobulins may be from any animal origin including birds and mammals. Preferably, the antibodies are human, rodent (e.g., mouse and rat), donkey, sheep, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example, in U.S. Pat. No. 5,939,598 by Kucherlapati et al.

The stabilized antibodies of the present invention may be monospecific, bispecific, trispecific or of greater multispecificity. Multispecific antibodies may be specific for different epitopes of a polypeptide or may be specific for heterologous epitopes, such as a heterologous polypeptide or solid support material. See, e.g., PCT publications WO 93/17715; WO 92/08802; WO 91/00360; WO 92/05793; Tutt, et al., *J. Immunol.,* 147:60-69, 1991; U.S. Pat. Nos. 4,474,893; 4,714,681; 4,925,648; 5,573,920; 5,601,819; Kostelny et al., *J. Immunol.,* 148:1547-1553, 1992.

The stabilized antibodies of the invention include derivatives that are otherwise modified, i.e., by the covalent attachment of any type of molecule to the antibody such that covalent attachment does not prevent the antibody from binding antigen and/or generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated herein by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, F(ab')$_2$ fragments may be produced by proteolytic cleavage of immunoglobulin molecules, using enzymes such as pepsin. F(ab')$_2$ fragments contain the complete light chain, and the variable region, the CH1 region and the hinge region of the heavy chain.

For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., *J. Immunol. Methods,* 182:41-50, 1995; Ames et al., *J. Immunol. Methods,* 184:177-186, 1995; Kettleborough et al., *Eur. J. Immunol.,* 24:952-958, 1994; Persic et al, *Gene,* 187:9-18, 1997; Burton et al., *Advances in Immunology,* 57:191-280, 1994; PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., *BioTechniques,* 12(6):864-869, 1992; and Sawai et al., *AJRI,* 34:26-34, 1995; and Better et al., *Science,* 240:1041-1043, 1988 (each of which is incorporated by reference in its entirety). Examples of techniques which can be used to produce single-chain Fvs and antibodies include those described in U.S. Pat. Nos. 4,946,778 and 5,258,498; Huston et al., *Methods in Enzymology,* 203:46-88, 1991; Shu et al., PNAS, 90:7995-7999, 1993; and Skerra et al., *Science,* 240:1038-1040, 1988.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, *Science,* 229:1202, 1985; Oi et al., *BioTechniques,* 4:214 1986; Gillies et al., *J. Immunol. Methods,* 125:191-202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., *Nature,* 332:323, 1988, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, *Molecular Immunology,* 28(4/5):489-498, 1991; Studnicka et al., *Protein Engineering,* 7(6):805-814, 1994; Roguska et al., *Proc Natl. Acad. Sci. USA,* 91:969-973, 1994), and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, *Int. Rev. Immunol.,* 13:65-93, 1995. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Pat. No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Freemont, Calif.) and Medarex (New Jersey) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology,* 12:899-903, 1988).

In particular embodiments, the stabilized antibodies have in vivo therapeutic and/or prophylactic uses. Examples of therapeutic and prophylactic antibodies which may be stabilized by the methods described herein include, but are not limited to, SYNAGIS® (MedImmune, Maryland) which is a humanized anti-respiratory syncytial virus (RSV) monoclonal antibody for the treatment of patients with RSV infection; HERCEPTIN® (Trastuzumab) (Genentech, California) which is a humanized anti-HER2 monoclonal antibody for the treatment of patients with metastatic breast cancer; REMICADE® (infliximab) (Centocor, Pennsylvania) which is a chimeric anti-TNFα monoclonal antibody for the treatment of patients with Crone's disease; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')$_2$ (Celltech, UK); PRO542 which is an anti- HIV gp120 antibody fused with CD4 (Progenics/Genzyme Transgenics); Ostavir which is a human anti Hepatitis B virus antibody (Protein Design Lab/Novartis); PROTOVIR™ which is a humanized anti-CMV IgG1 antibody (Protein Design Lab/Novartis); MAK-195 (SEGARD) which is a murine anti-TNF-α F(ab')$_2$ (Knoll Pharma/BASF); IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genetech/Xoma); ICM3 is a humanized anti-ICAM3 antibody (ICOS Pharm); IDEC-114 is a primatied anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); Ortho-Clone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/Norvartis/ Tanox Biosystems); IDEC-152 is a primatized anti-CD23 antibody (IDEC Pharm); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab')$_2$ (Pasteur-Merieux/Immunotech); CAT-152 is a human anti-TGF-β$_2$ antibody (Cambridge Ab Tech); Corsevin M is a chimeric anti-Factor VII antibody (Centocor); and Medi-507 (Siplizumab) is a humanized anti-CD2 IgG1 antibody (Medimmune, Inc.).

In specific embodiments, the invention provides stabilized antibodies having one or more of the stabilizing mutations described herein and that immunospecifically bind RSV, e.g., SYNAGIS®. The present invention also provides stabilized antibodies having one or more of the mutations described herein and that comprise a variable heavy (VH) and/or variable light (VL) domain having the amino acid sequence of any VH and/or VL domain listed in Table III. The present invention further encompasses stabilized anti-RSV antibodies comprising one or more VH complementarity determining regions (CDRs) and/or one or more VL CDRs having the amino acid sequence of one or more VH CDRs and/or VL CDRS listed in Table III or one or more of the CDRs listed in Table II wherein one or more of the bolded and underlined residues has an amino acid substitution, preferably that increases the affinity of the antibody for RSV. In specific embodiments, the antibody to be modified is AFFF, p12f2, p12f4, p11d4, Ale109, A12a6, A13c4, A17d4, A4B4, A8C7, 1X-493L1FR, H3-3F4, M3H9, Y10H6, DG, AFFF(1), 6H8, L1-7E5, L215B10, A13A11, A1H5, A4B4(1), A4B4L1FR-S28R, A4B4-F52S.

TABLE II

| CDR Sequences of SYNAGIS ® | | |
|---|---|---|
| CDR | Sequence | SEQ ID NO: |
| VH1 | TSGMSVG | 1 |
| VH2 | DIWWDDKKDYNPSLKS | 2 |
| VH3 | SMITNWYFDV | 3 |
| VL1 | KCQLSVGYMH | 4 |
| VL2 | DTSKLAS | 5 |
| VL3 | FQGSGYPFT | 6 |

TABLE III

ANTI-RSV ANTIBODIES

| Antibody Name | VH Domain | VH CDR1 | VH CDR2 | VH CDR3 | VL Domain | VL CDR1 | VL CDR2 | VL CDR3 |
|---|---|---|---|---|---|---|---|---|
| SYNAGIS | SEQ ID NO:7 | TSGMSVG (SEQ ID NO:1) | DIWWDDKKDYNPSLKS (SEQ ID NO:2) | SMITNWYFDV (SEQ ID NO:3) | SEQ ID NO:8 | KCQLSVGYMH (SEQ ID NO:4) | DTSKLAS (SEQ ID NO:5) | FQGSGYPFT (SEQ ID NO:6) |
| AFFF | SEQ ID NO:9 | TAGMSVG (SEQ ID NO:10) | DIWWDDKKDYNPSLKS (SEQ ID NO:2) | SMITNFYFDV (SEQ ID NO:12) | SEQ ID NO:13 | SASSSVGYMH (SEQ ID NO:14) | DTFKLAS (SEQ ID NO:15) | FQFSGYPFT (SEQ ID NO:16) |

TABLE III-continued

ANTI-RSV ANTIBODIES

| Antibody Name | VH Domain | VH CDR1 | VH CDR2 | VH CDR3 | VL Domain | VL CDR1 | VL CDR2 | VL CDR3 |
|---|---|---|---|---|---|---|---|---|
| p12f2 | SEQ ID NO:17 | TPGMSVG (SEQ ID NO:18) | DIWWDDKKHYNPSLKD (SEQ ID NO:19) | DMIFNFYFDV (SEQ ID NO:20) | SEQ ID NO:21 | SLSSRVGYMH (SEQ ID NO:22) | DTFYLSS (SEQ ID NO:23) | FQGSGYPFT (SEQ ID NO:6) |
| p12f4 | SEQ ID NO:24 | TPGMSVG (SEQ ID NO:18) | DIWWGKKHYNPSLKD (SEQ ID NO:25) | DMIFNFYFDV (SEQ ID NO:20) | SEQ ID NO:26 | SLSSRVGYMH (SEQ ID NO:22) | DTRGLPS (SEQ ID NO:27) | FQGSGYPFT (SEQ ID NO:6) |
| p11d4 | SEQ ID NO:28 | TPGMSVG (SEQ ID NO:18) | DIWWGKKHYNPSLKD (SEQ ID NO:25) | DMIFNWYFDV (SEQ ID NO:29) | SEQ ID NO:30 | SPSSRVGYMH (SEQ ID NO:31) | DTMRLAS (SEQ ID NO:32) | FQGSGYPFT (SEQ ID NO:6) |
| A1e109 | SEQ ID NO:33 | TAGMSVG (SEQ ID NO:10) | DIWWGKKHYNPSLKD (SEQ ID NO:25) | DMIFNWYFDV (SEQ ID NO:29) | SEQ ID NO:34 | SLSSRVGYMH (SEQ ID NO:22) | DTFKLSS (SEQ ID NO:35) | FQGSGYPFT (SEQ ID NO:6) |
| A12a6 | SEQ ID NO:36 | TAGMSVG (SEQ ID NO:10) | DIWWGKKDYNPSLKD (SEQ ID NO:37) | DMIFNFYFDV (SEQ ID NO:20) | SEQ ID NO:38 | SASSRVGYMH (SEQ ID NO:39) | DTFKLSS (SEQ ID NO:35) | FQGSGYPFT (SEQ ID NO:6) |
| A13c4 | SEQ ID NO:40 | TAGMSVG (SEQ ID NO:10) | DIWWGKKSYNPSLKD (SEQ ID NO:41) | DMIFNFYFDV (SEQ ID NO:20) | SEQ ID NO:42 | SLSSRVGYMH (SEQ ID NO:22) | DTMYQSS (SEQ ID NO:43) | FQGSGYPFT (SEQ ID NO:6) |
| A17d4 | SEQ ID NO:44 | TAGMSVG (SEQ ID NO:10) | DIWWDDKKSYNPSLKD (SEQ ID NO:45) | DMIFNFYFDV (SEQ ID NO:20) | SEQ ID NO:46 | LPSSRVGYMH (SEQ ID NO:47) | DTMYQSS (SEQ ID NO:43) | FQGSGYPFT (SEQ ID NO:6) |
| A4B4 | SEQ ID NO:48 | TAGMSVG (SEQ ID NO:10) | DIWWDDKKHYNPSLKD (SEQ ID NO:19) | DMIFNFYFDV (SEQ ID NO:20) | SEQ ID NO:49 | SASSRVGYMH (SEQ ID NO:39) | DTFFLDS (SEQ ID NO:50) | FQGSGYPFT (SEQ ID NO:6) |
| A8C7 | SEQ ID NO:51 | TAGMSVG (SEQ ID NO:10) | DIWWDDKKSYNPSLKD (SEQ ID NO:45) | DMIFNWYFDV (SEQ ID NO:29) | SEQ ID NO:52 | SPSSRVGYMH (SEQ ID NO:31) | DTRYQSS (SEQ ID NO:53) | FQGSGYPFT (SEQ ID NO:6) |
| 1X-493L1FR | SEQ ID NO:7 | TSGMSVG (SEQ ID NO:1) | DIWWDDKKDYNPSLKS (SEQ ID NO:2) | SMITNWYFDV (SEQ ID NO:3) | SEQ ID NO:54 | SASSSVGYMH (SEQ ID NO:14) | DTSKLAS (SEQ ID NO:5) | FQGSGYPFT (SEQ ID NO:6) |
| H3-3F4 | SEQ ID NO:55 | TAGMSVG (SEQ ID NO:10) | DIWWDDKKDYNPSLKS (SEQ ID NO:2) | DMIFNWYFDV (SEQ ID NO:29) | SEQ ID NO:56 | SASSSVGYMH (SEQ ID NO:14) | DTFKLAS (SEQ ID NO:15) | FQGSGYPFT (SEQ ID NO:6) |
| M3H9 | SEQ ID NO:55 | TAGMSVG (SEQ ID NO:10) | DIWWDDKKDYNPSLKS (SEQ ID NO:2) | DMIFNWYFDV (SEQ ID NO:29) | SEQ ID NO:56 | SASSSVGYMH (SEQ ID NO:14) | DTYQTS (SEQ ID NO:57) | FQGSGYPFT (SEQ ID NO:6) |
| Y10H6 | SEQ ID NO:55 | TAGMSVG (SEQ ID NO:10) | DIWWDDKKDYNPSLKS (SEQ ID NO:2) | DMIFNWYFDV (SEQ ID NO:29) | SEQ ID NO:58 | SASSSVGYMH (SEQ ID NO:14) | DTRYLSS (SEQ ID NO:59) | FQGSGYPFT (SEQ ID NO:6) |
| DG | SEQ ID NO:78 | TAGMSVG (SEQ ID NO:10) | DIWWDDKKDYNPSLKS (SEQ ID NO:2) | DMITNFYFDV (SEQ ID NO:79) | SEQ ID NO:56 | SASSSVGYMH (SEQ ID NO:14) | DTFKLAS (SEQ ID NO:15) | FQGSGYPFT (SEQ ID NO:6) |
| AFFF(1) | SEQ ID NO:9 | TAGMSVG (SEQ ID NO:10) | DIWWDDKKDYNPSLKS (SEQ ID NO:2) | SMITNFYFDV (SEQ ID NO:12) | SEQ ID NO:60 | SASSSVGYMH (SEQ ID NO:14) | DTFKLAS (SEQ ID NO:15) | FQGSFYPFT (SEQ ID NO:61) |
| 6H8 | SEQ ID NO:78 | TAGMSVG (SEQ ID NO:10) | DIWWDDKKDYNPSLKS (SEQ ID NO:2) | DMITNFYFDV (SEQ ID NO:79) | SEQ ID NO:62 | SASSSVGYMH (SEQ ID NO:14) | DTFKLTS (SEQ ID NO:63) | FQGSGYPFT (SEQ ID NO:6) |
| L1-7E5 | SEQ ID NO:78 | TAGMSVG (SEQ ID NO:10) | DIWWDDKKDYNPSLKS (SEQ ID NO:2) | DMITNFYFDV (SEQ ID NO:79) | SEQ ID NO:64 | SASSRVGYMH (SEQ ID NO:39) | DTFKLAS (SEQ ID NO:15) | FQGSGYPFT (SEQ ID NO:6) |
| L215B10 | SEQ ID NO:78 | TAGMSVG (SEQ ID NO:10) | DIWWDDKKDYNPSLKS (SEQ ID NO:2) | DMITNFYFDV (SEQ ID NO:79) | SEQ ID NO:65 | SASSSVGYMH (SEQ ID NO:14) | DTFRLAS (SEQ ID NO:66) | FQGSGYPFT (SEQ ID NO:6) |

TABLE III-continued

ANTI-RSV ANTIBODIES

| Antibody Name | VH Domain | VH CDR1 | VH CDR2 | VH CDR3 | VL Domain | VL CDR1 | VL CDR2 | VL CDR3 |
|---|---|---|---|---|---|---|---|---|
| A13A11 | SEQ ID NO:67 | TAGMSVG (SEQ ID NO:10) | DIWWDDKKHYNPSLKD (SEQ ID NO:19) | DMIFNWYFDV (SEQ ID NO:29) | SEQ ID NO:68 | SPSSRVGYMH (SEQ ID NO:31) | DTYRHSS (SEQ ID NO:69) | FQGSGYPFT (SEQ ID NO:6) |
| A1H5 | SEQ ID NO:70 | TAGMSVG (SEQ ID NO:10) | DIWWDGKKHYNPSLKD (SEQ ID NO:25) | DMIFNWYFDV (SEQ ID NO:29) | SEQ ID NO:71 | SLSSSVGYMH (SEQ ID NO:72) | DTFFHRS (SEQ ID NO:73) | FQGSGYPFT (SEQ ID NO:6) |
| A4B4(1) | SEQ ID NO:48 | TAGMSVG (SEQ ID NO:10) | DIWWDDKKHYNPSLKD (SEQ ID NO:19) | DMIFNFYFDV (SEQ ID NO:20) | SEQ ID NO:74 | SASSRVGYMH (SEQ ID NO:39) | DTLLLDS (SEQ ID NO:75) | FQGSGYPFT (SEQ ID NO:6) |
| A4B4L1FR-S28R | SEQ ID NO:48 | TAGMSVG (SEQ ID NO:10) | DIWWDDKKHYNPSLKD (SEQ ID NO:19) | DMIFNFYFDV (SEQ ID NO:20) | SEQ ID NO:11 | SASSRVGYMH (SEQ ID NO:39) | DTSKLAS (SEQ ID NO:5) | FQGSGYPFT (SEQ ID NO:6) |
| A4B4-F52S | SEQ ID NO:48 | TAGMSVG (SEQ ID NO:10) | DIWWDDKKHYNPSLKD (SEQ ID NO:19) | DMIFNFYFDV (SEQ ID NO:20) | SEQ ID NO:76 | SASSRVGYMH (SEQ ID NO:39) | DTSFLDS (SEQ ID NO:77) | FQGSGYPFT (SEQ ID NO:6) |

In other embodiments, the antibody is a stabilized anti-$\alpha_v\beta_3$ antibody, preferably a Vitaxin antibody (see, PCT publications WO 98/33919 and WO 00/78815, both by Huse et al., and both of which are incorporated by reference herein in their entireties).

Stabilized IgGs of the present invention also include IgGs whose bioactive sites, such as antigen-binding sites, Fc-receptor binding sites, or complement-binding sites, are modified by genetic engineering to increase or reduce such activities compared to the wild type.

Stabilization of these and other therapeutic antibodies to increase the storage stability and/or in vivo half-life permits longer term storage, less stringent storage conditions, administration of lower effective dosages and/or less frequent dosing of the therapeutic antibody.

The present invention further comprises stabilized glycoproteins, more specifically stabilized immunoglobulins, covalently joined or conjugated to a bioactive molecule. The bioactive molecule can be a therapeutic moiety such as a cytotoxin (e.g., a cytostatic or cytocidal agent), a therapeutic agent or a radioactive element (e.g., alpha-emitters, gamma-emitters, etc.).

The present invention also provides polynucleotides comprising a nucleotide sequence encoding a stabilized immunoglobulin of the invention and vectors comprising said polynucleotides.

The nucleotide sequence of stabilized IgGs and the polynucleotides encoding the same may be obtained by any methods known in the art, including general DNA sequencing method, such as dideoxy chain termination method (Sanger sequencing), and oligonucleotide priming in combination with PCR, respectively.

5.5. Recombinant Methods of Producing Stabilized Glycoproteins

The stabilized glycoproteins of the invention can be produced by any method known in the art for the protein synthesis, in particular, by chemical synthesis or preferably, by recombinant expression techniques. Stabilized glycoproteins of the invention that are antibodies or immunoglobulins can be produced by any method known in the art for antibody or immunoglobulin synthesis, in particular by chemical synthesis or, more preferably, by recombinant expression techniques.

The nucleotide sequence encoding a non-stabilized counterpart of a stabilized antibody may be obtained from any information available to those of skill in the art (i.e., from Genbank, the literature, or by routine cloning). If a clone containing a nucleic acid encoding a particular antibody or an epitope-binding fragment thereof is not available, but the sequence of the antibody molecule or epitope-binding fragment thereof is known, a nucleic acid encoding the immunoglobulin may be chemically synthesized or obtained from a suitable source (e.g., an antibody cDNA library, or a cDNA library generated from, or nucleic acid, preferably poly A$^+$RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual*, 2d Ed., Cold Spring Harbor Laboratory, Cold Spring Harbor, N.Y.; and Ausubel et al., eds., 1998, *Current Protocols in Molecular Biology*, John Wiley & Sons, New York, which are both incorporated by reference herein in their entireties), to generate antibodies having a different amino acid sequence (other than the stabilizing modification(s)) by, for example, introducing amino acid substitutions, deletions, and/or insertions into the epitope-binding domain regions of the antibodies. Additionally, the nucleic acids can be manipulated to introduce stabilizing mutations into the encoded antibodies.

In a preferred embodiment, stabilized antibodies having one or more modifications in Kabat amino acid residues 233-239 and/or 249 are generated.

Recombinant expression of a stabilized antibody requires construction of an expression vector containing a nucleotide sequence that encodes the antibody. Once a nucleotide sequence encoding a stabilized antibody molecule or a heavy or light chain of an antibody, or portion thereof (preferably, but not necessarily, containing the heavy or light chain variable region) has been obtained, the vector for the production of the antibody molecule may be produced by recombinant DNA technology using techniques well known in the art. Thus, methods for preparing a protein by expressing a polynucleotide containing a stabilized antibody-encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding the stabilized immunoglobulins of the present invention (see, e.g., PCT Publication WO 86/05807; PCT Publication WO 89/01036; and U.S. Pat. No. 5,122,464). The nucleotide sequence encoding the heavy-chain variable region, light-chain variable region, both the heavy-chain and light-chain variable regions, an epitope-binding fragment of the heavy- and/or light-chain variable region, or one or more complementarity determining regions (CDRs) of an antibody may be cloned into such a vector for expression.

The expression vector is transferred to a host cell by conventional techniques and the transfected cells are then cultured by conventional techniques to produce a stabilized antibody. Thus, the invention includes host cells containing a polynucleotide encoding a stabilized immunoglobulin, i.e., an immunoglobulin having one or more stabilizing modifications, for example one ore more stabilizing point mutations in amino acid residues 233-239 and/or 249, preferably, operably linked to a heterologous promoter.

A variety of host-expression vector systems may be utilized to express the stabilized antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces* and *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; and tobacco mosaic virus, TMV) or transformed with recombinant plasmid expression vectors (e.g., Ti plasmid) containing antibody coding sequences; and mammalian cell systems (e.g., COS, CHO, BHK, 293, 3T3 and NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene*, 45:101, 1986, and Cockett et al., *Bio/Technology*, 8:2, 1990).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO*, 12:1791, 1983), in which the antibody coding sequence may be ligated individually into the vector in frame with the lacZ coding region so that a fusion protein is produced; and pIN vectors (Inouye & Inouye, *Nucleic Acids Res.*, 13:3101-3109, 1985 and Van Heeke & Schuster, *J. Biol. Chem.*, 24:5503-5509, 1989).

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized to express an antibody molecule of the invention. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA*, 81:355-359, 1984). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bitter et al., *Methods in Enzymol.*, 153:516-544, 1987).

In addition, a host cell strain may be chosen which modulates the expression of the antibody sequences, or modifies and processes the antibody in the specific fashion desired. Such modifications (e.g., glycosylation) and processing (e.g., cleavage) of protein products may be important for the function of the antibody. Different host cells have characteristic and specific mechanisms for the post-translational processing and modification of proteins and gene products. Appropriate cell lines or host systems can be chosen to ensure the correct modification and processing of the antibody expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, W138, and in particular, myeloma cells such as NS0 cells, and related cell lines, see, for example, Morrison et al., U.S. Pat. No. 5,807,715, which is hereby incorporated by reference in its entirety.

For long-term, high-yield production of recombinant antibodies, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., *Cell,* 11:223, 1977), hypoxanthineguanine phosphoribosyltransferase (Szybalska & Szybalski, *Proc. Natl. Acad. Sci. USA,* 48:202, 1992), and adenine phosphoribosyltransferase (Lowy et al., *Cell,* 22:8-17, 1980) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., *Natl. Acad. Sci. USA,* 77:357, 1980 and O'Hare et al., *Proc. Natl. Acad. Sci. USA,* 78:1527, 1981); gpt, which confers resistance to mycophenolic acid (Mulligan & Berg, *Proc. Natl. Acad. Sci. USA,* 78:2072, 1981); neo, which confers resistance to the aminoglycoside G-418 (Wu and Wu, *Biotherapy,* 3:87-95, 1991; Tolstoshev, *Ann. Rev. Pharmacol. Toxicol.,* 32:573-596, 1993; Mulligan, *Science,* 260:926-932, 1993; and Morgan and Anderson, *Ann. Rev. Biochem.,* 62: 191-217, 1993; and May, *TIB TECH,* 11(5):155-215, 1993); and hygro, which confers resistance to hygromycin (Santerre et al., *Gene,* 30:147, 1984). Methods commonly known in the art of recombinant DNA technology may be routinely applied to select the desired recombinant clone, and such methods are described, for example, in Ausubel et al. (eds.), 1993, *Current Protocols in Molecular Biology,* John Wiley & Sons, New York; Kriegler, 1990, *Gene Transfer and Expression, A Laboratory Manual,* Stockton Press, New York; in Chapters 12 and 13, Dracopoli et al. (eds), 1994, *Current Protocols in Human Genetics,* John Wiley & Sons, New York; and Colberre-Garapin et al., *J. Mol. Biol.,* 150:1, 1981, which are incorporated by reference herein in their entireties.

The expression levels of an antibody molecule can be increased by vector amplification (for a review, see Bebbington and Hentschel, 1987, *The use of vectors based on gene amplification for the expression of cloned genes in mammalian cells in DNA cloning,* Vol. 3. Academic Press, New York). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol., Cell. Biol.,* 3:257, 1983).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature,* 322:52, 1986; and Kohler, *Proc. Natl. Acad. Sci. USA,* 77:2 197, 1980). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A purification, and sizing column chromatography), centrifugation, differential solubility, or by any other standard techniques for the purification of proteins. Further, the antibodies of the present invention or fragments thereof may be fused to heterologous polypeptide sequences described herein or otherwise known in the art to facilitate purification.

5.5.1. Antibody Conjugates

As mentioned supra, the present invention encompasses modified glycoproteins recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences. Stabilized antibodies fused or conjugated to heterologous polypeptides may also be used in in vitro immunoassays and purification methods using methods known in the art. See e.g., PCT Publication No. WO 93/21232; EP 439,095; Naramura et al., *Immunol. Lett.,* 39:91-99, 1994; U.S. Pat. No. 5,474,981; Gillies et al., *PNAS,* 89:1428-1432, 1992; and Fell et al., *J. Immunol.,* 146:2446-2452, 1991, which are incorporated herein by reference in their entireties.

Stabilized antibodies can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA,* 86:821-824, 1989, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., *Cell,* 37:767 1984) and the "flag" tag (Knappik et al., *Biotechniques,* 17(4):754-761, 1994).

The present invention also encompasses stabilized antibodies conjugated to a diagnostic or therapeutic agent or any other molecule for which storage stability and/or in vivo half-life is desired to be increased. The antibodies can be used diagnostically to, for example, monitor the development or progression of a disease, disorder or infection as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99m}$Tc.

A stabilized antibody may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, a stabilized antibody may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, PCT Publication No. WO 97/34911), Fas Ligand (Takahashi et al., J. Iminunol., 6:1567-1574, 1994), and VEGI (PCT Publication No. WO 99/23105), a thrombotic agent or an anti-angiogenic agent (e.g., angiostatin or endostatin); or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Techniques for conjugating such therapeutic moieties to antibodies are well known; see, e.g., Arnon et al., "Monoclonal Antibodies For Immunotargeting Of Drugs In Cancer Therapy", in *Monoclonal Antibodies And Cancer Therapy*, Reisfeld et al. (eds.), 1985, pp. 243-56, Alan R. Liss, Inc.); Hellstrom et al., "Antibodies For Drug Delivery", in *Controlled Drug Delivery* (2nd Ed.), Robinson et al. (eds.), 1987, pp. 623-53, Marcel Dekker, Inc.); Thorpe, "Antibody Carriers Of Cytotoxic Agents In Cancer Therapy: A Review", in *Monoclonal Antibodies '84: Biological And Clinical Applications*, Pinchera et al. (eds.), 1985, pp. 475-506); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.),1985, pp. 303-16, Academic Press; and Thorpe et al., *Immunol. Recombinant expression vector.*, 62:119-58, 1982.

A stabilized antibody or fragment thereof, with or without a therapeutic moiety conjugated to it, administered alone or in combination with cytotoxic factor(s) and/or cytokine(s) can be used as a therapeutic.

Alternatively, a stabilized antibody can be conjugated to a second antibody, which is preferably also a stabilized antibody, to form an antibody heteroconjugate as described by Segal in U.S. Pat. No. 4,676,980, which is incorporated herein by reference in its entirety.

Stabilized antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.6. Methods of Producing Fusion Proteins

Fusion proteins can be produced by standard recombinant DNA techniques or by protein synthetic techniques, e.g., by use of a peptide synthesizer. For example, a nucleic acid molecule encoding a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992). Moreover, a nucleic acid encoding a bioactive molecule can be cloned into an expression vector containing the Fc domain or a fragment thereof such that the bioactive molecule is linked in-frame to the constant domain or fragment thereof.

Methods for fusing or conjugating polypeptides to the constant regions of antibodies are known in the art. See, e.g., U.S. Pat. Nos. 5,336,603, 5,622,929, 5,359,046, 5,349,053, 5,447, 851, 5,723,125, 5,783,181, 5,908,626, 5,844,095, and 5,112, 946; EP 307,434; EP 367,166; EP 394,827; PCT publications WO 91/06570, WO 96/04388, WO 96/22024, WO 97/34631, and WO 99/04813; Ashkenazi et al., *Proc. Natl. Acad. Sci. USA*, 88: 10535-10539, 1991; Traunecker et al., *Nature*, 331: 84-86, 1988; Zheng et al., *J. Immunol.*, 154:5590-5600, 1995; and Vil et al., *Proc. Natl. Acad. Sci. USA*, 89:11337-11341, 1992, which are incorporated herein by reference in their entireties.

The nucleotide sequence encoding a bioactive molecule may be obtained from any information available to those of skill in the art (e.g., from Genbank, the literature, or by routine cloning), and the nucleotide sequence encoding a stabilized antibody may be determined by sequence analysis of mutants produced using techniques described herein, or may be obtained from Genbank or the literature. The nucleotide sequence coding for a fusion protein can be inserted into an appropriate expression vector, i.e., a vector which contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The expression of a fusion protein may be controlled by any promoter or enhancer element known in the art. Promoters which may be used to control the expression of the gene encoding fusion protein include, but are not limited to, the SV40 early promoter region (Bernoist and Chambon, *Nature*, 290:304-310, 1981), the promoter contained in the 3' long terminal repeat of Rous sarcoma virus (Yamamoto, et al., *Cell*, 22:787-797, 1980), the herpes thymidine kinase promoter (Wagner et al., *Proc. Natl. Acad. Sci. U.S.A.*, 78:1441-1445, 1981), the regulatory sequences of the metallothionein gene (Brinster et al., *Nature*, 296:39-42, 1982), the tetracycline (Tet) promoter (Gossen et al., *Proc. Nat. Acad. Sci. USA*, 89:5547-5551, 1995); prokaryotic expression vectors such as the β-lactamase promoter (Villa-Kamaroff, et al., *Proc. Natl. Acad. Sci. U.S.A.*, 75:3727-3731, 1978), or the tac promoter (DeBoer, et al., *Proc. Natl. Acad. Sci. U.S.A.*, 80:21-25, 1983; see also "Useful proteins from recombinant bacteria" in *Scientific American*, 242:74-94, 1980); plant expression vectors comprising the nopaline synthetase promoter region (Herrera-Estrella et al., *Nature*, 303:209-213, 1983) or the cauliflower mosaic virus 35S RNA promoter (Gardner, et al., *Nucl. Acids Res.*, 9:2871, 1981), and the promoter of the photosynthetic enzyme ribulose biphosphate carboxylase (Herrera-Estrella et al., *Nature*, 310:115-120, 1984); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., *Cell* 38:639-646, 1984; Ornitz et al., 50:399-409, *Cold Spring Harbor Symp. Quant. Biol.*, 1986; MacDonald, *Hepatology* 7:425-515, 1987); insulin gene control region which is active in pancreatic beta cells (Hanahan, *Nature* 315:115-122, 1985), immunoglobulin gene control region which is active in lymphoid cells (Grosschedl et al., *Cell*, 38:647-658, 1984; Adames et al., *Nature* 318:533-538, 1985; Alexander et al., *Mol. Cell. Biol.*, 7:1436-1444, 1987), mouse mammary tumor virus control region which is active in testicular, breast, lymphoid and mast cells (Leder et al., *Cell*, 45:485-495, 1986), albumin gene control region which is active in liver (Pinkert et al., *Genes and Devel.*, 1:268-276, 1987), α-fetoprotein gene control region which is active in liver (Krumlauf et al., *Mol. Cell. Biol.*, 5:1639-1648, 1985; Hammer et al., *Science*, 235:53-58, 1987; α 1-antitrypsin gene control region which is active in the liver (Kelsey et al., *Genes and Devel.*, 1:161-171, 1987), beta-globin gene control region which is active in myeloid cells (Mogram et al., *Nature*, 315:338-340, 1985; Kollias et al., *Cell*, 46:89-94, 1986; myelin basic protein gene control region which is active in oligodendrocyte cells in the brain (Readhead et al., *Cell*, 48:703-712, 1987); myosin light chain-2 gene control region which is active in skeletal muscle (Sani, *Nature*, 314:283-286, 1985); neuronal-specific enolase (NSE) which is active in neuronal cells (Morelli et al., *Gen. Virol.*, 80:571-83, 1999); brain-derived neurotrophic factor (BDNF) gene control region which is active in neuronal cells (Tabuchi et al., *Biochem. Biophysic. Res. Comprising.*, 253: 818-823, 1998); glial fibrillary acidic protein (GFAP) promoter which is active in astrocytes (Gomes et al., Braz. J. Med. Biol. Res., 32(5):619-631, 1999; Morelli et al., *Gen. Virol.*, 80:571-83, 1999) and gonadotropic releasing hormone gene control region which is active in the hypothalamus (Mason et al., *Science*, 234:1372-1378, 1986).

In a specific embodiment, the expression of a fusion protein is regulated by a constitutive promoter. In another embodiment, the expression of a fusion protein is regulated by an inducible promoter. In accordance with these embodiments, the promoter may be a tissue-specific promoter.

In a specific embodiment, a vector is used that comprises a promoter operably linked to a fusion protein-encoding nucleic acid, one or more origins of replication, and, optionally, one or more selectable markers (e.g., an antibiotic resistance gene).

In mammalian host cells, a number of viral-based expression systems may be utilized. In cases where an adenovirus is used as an expression vector, the fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA*, 81:355-359, 1984). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., *Methods in Enzymol.*, 153:516-544, 1987).

Expression vectors containing inserts of a gene encoding a fusion protein can be identified by three general approaches: (a) nucleic acid hybridization, (b) presence or absence of "marker" gene functions, and (c) expression of inserted sequences. In the first approach, the presence of a gene encoding a fusion protein in an expression vector can be detected by nucleic acid hybridization using probes comprising sequences that are homologous to an inserted gene encoding the fusion protein. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (i.e., fusion protein)

expressed by the recombinant. Such assays can be based, for example, on the physical or functional properties of the fusion protein in in vitro assay systems.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, WI38, and in particular, neuronal cell lines such as, for example, SK-N-AS, SK-N-FI, SK-N-DZ human neuroblastomas (Sugimoto et al., *J. Natl. Cancer Inst.*, 73: 51-57, 1984), SK-N-SH human neuroblastoma (*Biochim. Biophys. Acta*, 704: 450-460, 1982), Daoy human cerebellar medulloblastoma (He et al., *Cancer Res.*, 52: 1144-1148, 1992) DBTRG-05MG glioblastoma cells (Kruse et al., 1992, *In Vitro Cell. Dev. Biol.*, 28A: 609-614, 1992), IMR-32 human neuroblastoma (*Cancer Res.*, 30: 2110-2118, 1970), 1321N1 human astrocytoma (*Proc. Natl Acad. Sci. USA*, 74: 4816, 1997), MOG-G-CCM human astrocytoma (Br. J. Cancer, 49: 269, 1984), U87MG human glioblastoma-astrocytoma (*Acta Pathol. Microbiol. Scand.*, 74: 465-486, 1968), A172 human glioblastoma (Olopade et al., *Cancer Res.*, 52: 2523-2529, 1992), C6 rat glioma cells (Benda et al., Science, 161: 370-371, 1968), Neuro-2a mouse neuroblastoma (*Proc. Natl. Acad. Sci. USA*, 65: 129-136, 1970), NB41A3 mouse neuroblastoma (*Proc. Natl. Acad. Sci. USA*, 48: 1184-1190, 1962), SCP sheep choroid plexus (Bolin et al., *J. Virol. Methods*, 48: 211-221, 1994), G355-5, PG-4 Cat normal astrocyte (Haapala et al., *J. Virol.*, 53: 827-833, 1985), Mpf ferret brain (Trowbridge et al., *In Vitro*, 18: 952-960, 1982), and normal cell lines such as, for example, CTX TNA2 rat normal cortex brain (Radany et al., *Proc. Natl. Acad. Sci. USA*, 89: 6467-6471, 1992) such as, for example, CRL7030 and Hs578Bst. Furthermore, different vector/host expression systems may effect processing reactions to different degrees.

For long-term, high-yield production of recombinant proteins, stable expression is preferred. For example, cell lines which stably express the fusion protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the fusion protein. Such engineered cell lines may be particularly useful in screening and evaluation of compounds that affect the endogenous activity of the fusion protein.

A number of selection systems may be used, including but not limited to the herpes simplex virus thymidine kinase (Wigler, et al., *Cell*, 11:223, 1997), hypoxanthine-guanine phosphoribosyltransferase (Szybalska & Szybalski, *Proc. Natl. Acad. Sci. USA*, 48:2026, 1962), and adenine phosphoribosyltransferase (Lowy, et al., 1980, *Cell*, 22:817, 1980) genes can be employed in tk-, hgprt- or aprt- cells, respectively. Also, antimetabolite resistance can be used as the basis of selection for dhfr, which confers resistance to methotrexate (Wigler, et al., *Natl. Acad. Sci. USA*, 77:3567, 1980; O'Hare, et al., *Proc. Natl. Acad. Sci. USA*, 78:1527, 1981); gpt, which confers resistance to mycophenolic acid (Mulligan & Berg, *Proc. Natl. Acad. Sci. USA*, 78:2072, 1981); neo, which confers resistance to the aminoglycoside G-418 (Colberre-Garapin, et al., *J. Mol. Biol.*, 150:1, 1981); and hygro, which confers resistance to hygromycin (Santerre, et al., *Gene*, 30:147, 1984) genes.

Once a fusion protein of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

5.7. Prophylactic and Therapeutic Uses of Stabilized Glycoproteins

The present invention encompasses glycoprotein-based therapies which involve administering stabilized glycoproteins to an animal, preferably a mammal and most preferably a human, for preventing, treating, or ameliorating symptoms associated with a disease, disorder, or infection. Prophylactic and therapeutic stabilized glycoproteins of the invention include, but are not limited to, antibodies, immunoglobulins, fusion proteins and nucleic acids encoding antibodies, immunoglobulins, fusion proteins and conjugated molecules. Stabilized glycoproteins may be provided in pharmaceutically acceptable compositions as known in the art or as described herein.

Stabilized glycoproteins of the present invention that function as antagonists of a disease, disorder, or infection can be administered to an animal, preferably a mammal, and most preferably a human, to treat, prevent or ameliorate one or more symptoms associated with the disease, disorder, or infection. Further, stabilized glycoproteins that function as agonists of the immune response may be administered to an animal, preferably a mammal, and most preferably a human, to treat, prevent or ameliorate one or more symptoms associated with the disease, disorder, or infection.

One or more stabilized glycoproteins may be used locally or systemically in the body as therapeutics. The stabilized glycoproteins of this invention may also be advantageously utilized in combination with monoclonal or chimeric antibodies, or with lymphokines or hematopoietic growth factors (such as, e.g., IL-2, IL-3 and IL-7), which, for example, serve to increase the number or activity of effector cells which interact with the antibodies. The stabilized glycoproteins of this invention may also be advantageously utilized in combination with monoclonal or chimeric antibodies, or with lymphokines or hematopoietic growth factors (such as, e.g., IL-2, IL-3 and IL-7), which, for example, serve to increase the immune response. The stabilized glycoproteins of this invention may also be advantageously utilized in combination with one or more drugs used to treat a disease, disorder, or infection such as, for example anti-cancer agents, anti-inflammatory agents or anti-viral agents. Examples of anti-cancer agents include, but are not limited to, isplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, and taxol. Examples of anti-viral agents include, but are not limited to, cytokines (e.g., IFN-α, IFN-β, IFN-γ), inhibitors of reverse transcriptase (e.g., AZT, 3TC, D4T, ddC, ddI, d4T, 3TC, adefovir, efavirenz, delavirdine, nevirapine, abacavir, and other dideoxynucleosides or dideoxyfluoronucleosides), inhibitors of viral mRNA capping, such as ribavirin, inhibitors of proteases such HIV protease inhibitors (e.g., amprenavir, indinavir, nelfinavir, ritonavir, and saquinavir,), amphotericin B, castanospermine as an inhibitor of glycoprotein processing, inhibitors of neuraminidase such as influenza virus neuraminidase inhibitors (e.g., zanamivir and oseltamivir), topoisomerase I inhibitors (e.g., camptothecins and analogs thereof), amantadine, and rimantadine. Examples of anti-inflammatory agents include, but are not limted to, nonsteroidal anti-inflammatory drugs such as COX-2 inhibitors (e.g., meloxicam, celecoxib, rofecoxib, flosulide, and SC-58635, and MK-966), ibuprofen and indomethacin, and steroids (e.g., deflazacort, dexamethasone and methylprednisolone).

In a specific embodiment, stabilized glycoproteins administered to an animal are of a species origin or species reactivity that is the same species as that of the animal. Thus, in a specific embodiment, human stabilized fusion proteins or human stabilized antibodies, or nucleic acids encoding human stabilized fusion proteins or human stabilized antibodies, are administered to a human subject for therapy or prophylaxis.

5.7.1. Prophylactic and Therapeutic Uses of Stabilized Antibodies

The present invention encompasses antibody-based therapies which involve administering stabilized antibodies to an animal, preferably a mammal, and most preferably a human, for preventing, treating, or ameliorating symptoms associated with a disease, disorder, or infection. Prophylactic and therapeutic compounds of the invention include, but are not limited to, stabilized antibodies and nucleic acids encoding stabilized antibodies. Stabilized antibodies may be provided in pharmaceutically acceptable compositions as known in the art or as described herein.

Stabilized antibodies of the present invention that function as antagonists of a disease, disorder, or infection can be administered to an animal, preferably a mammal and most preferably a human, to treat, prevent or ameliorate one or more symptoms associated with the disease, disorder, or infection. For example, stabilized antibodies which disrupt or prevent the interaction between a viral antigen and its host cell receptor may be administered to an animal, preferably a mammal and most preferably a human, to treat, prevent or ameliorate one or more symptoms associated with a viral infection.

In a specific embodiment, a stabilized antibody prevents a viral or bacterial antigen from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to antigen binding to its host cell receptor in the absence of said stabilized antibodies. In another embodiment, a combination of stabilized antibodies prevents a viral or bacterial antigen from binding to its host cell receptor by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to antigen binding to its host cell receptor in the absence of said stabilized antibodies. In a preferred embodiment, the stabilized antibody is used to treat or prevent RSV infection Stabilized antibodies which do not prevent a viral or bacterial antigen from binding its host cell receptor but inhibit or downregulate viral or bacterial replication can also be administered to an animal to treat, prevent or ameliorate one or more symptoms associated with a viral or bacterial infection. The ability of a stabilized antibody to inhibit or downregulate viral or bacterial replication may be determined by techniques described herein or otherwise known in the art. For example, the inhibition or downregulation of viral replication can be determined by detecting the viral titer in the animal.

In a specific embodiment, a stabilized antibody inhibits or downregulates viral or bacterial replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to viral or bacterial replication in absence of said stabilized antibody. In another embodiment, a combination of stabilized antibodies inhibits or downregulates viral or bacterial replication by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to viral or bacterial replication in absence of said stabilized antibodies.

Stabilized antibodies can also be used to prevent, inhibit or reduce the growth or metastasis of cancerous cells. In a specific embodiment, a stabilized antibody inhibits or reduces the growth or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of said stabilized antibody. In another embodiment, a combination of stabilized antibodies inhibits or reduces the growth or metastasis of cancer by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of said stabilized antibodies. Examples of cancers include, but are not limited to, leukemia (e.g., acute leukemia such as acute lymphocytic leukemia and acute myelocytic leukemia), neoplasms, tumors (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma), heavy chain disease, metastases, or any disease or disorder characterized by uncontrolled cell growth.

Stabilized antibodies can also be used to reduce the inflammation experienced by animals, particularly mammals, with inflammatory disorders. In a specific embodiment, a stabilized antibody reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in the not administered said stabilized antibody. In another embodiment, a combination of stabilized antibodies reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal in not administered said stabilized antibodies. Examples of inflammatory disorders include, but are not limited to, rheumatoid arthritis, spondyloarthropathies, inflammatory bowel disease and asthma.

In certain embodiments, the stabilized antibody used for treatment of inflammation (or cancer) is a stabilized anti-$\alpha_v\beta_3$ antibody, preferably a Vitaxin antibody (see, PCT publications WO 98/33919 and WO 00/78815, both by Huse et al., and both of which are incorporated by reference herein in their entireties).

Stabilized antibodies can also be used to prevent the rejection of transplants. Stabilized antibodies can also be used to prevent clot formation. Further, stabilized antibodies that function as agonists of the immune response can also be administered to an animal, preferably a mammal, and most preferably a human, to treat, prevent or ameliorate one or more symptoms associated with the disease, disorder, or infection.

One or more stabilized antibodies that immunospecifically bind to one or more antigens may be used locally or systemically in the body as a therapeutic. The stabilized antibodies of this invention may also be advantageously utilized in combination with other monoclonal or chimeric antibodies, or with lymphokines or hematopoietic growth factors (such as, e.g., IL-2, IL-3 and IL-7), which, for example, serve to increase the number or activity of effector cells which interact with the antibodies. The stabilized antibodies of this invention may also be advantageously utilized in combination with other monoclonal or chimeric antibodies, or with lymphokines or hematopoietic growth factors (such as, e.g., IL-2, IL-3 and IL-7), which, for example, serve to increase the immune response. The stabilized antibodies of this invention may also be advantageously utilized in combination with one or more drugs used to treat a disease, disorder, or infection such as, for example anti-cancer agents, anti-inflammatory agents or anti-viral agents. Examples of anti-cancer agents include, but are not limited to, isplatin, ifosfamide, paclitaxel, taxanes, topoisomerase I inhibitors (e.g., CPT-11, topotecan, 9-AC, and GG-211), gemcitabine, vinorelbine, oxaliplatin, 5-fluorouracil (5-FU), leucovorin, vinorelbine, temodal, and taxol. Examples of anti-viral agents include, but are not limited to, cytokines (e.g., IFN-$\alpha$, IFN-$\beta$, IFN-$\gamma$), inhibitors of reverse transcriptase (e.g., AZT, 3TC, D4T, ddC, ddI, d4T, 3TC, adefovir, efavirenz, delavirdine, nevirapine, abacavir, and other dideoxynucleosides or dideoxyfluoronucleosides), inhibitors of viral mRNA capping, such as ribavirin, inhibitors of proteases such HIV protease inhibitors (e.g., amprenavir, indinavir, nelfinavir, ritonavir, and saquinavir,), amphotericin B, castanospermine as an inhibitor of glycoprotein processing, inhibitors of neuraminidase such as influenza virus neuraminidase inhibitors (e.g., zanamivir and oseltamivir), topoisomerase I inhibitors (e.g., camptothecins and analogs thereof), amantadine, and rimantadine. Examples of anti-inflammatory agents include, but are not limited to, nonsteroidal anti-inflammatory drugs such as COX-2 inhibitors (e.g., meloxicam, celecoxib, rofecoxib, flosulide, and SC-58635, and MK-966), ibuprofen and indomethacin, and steroids (e.g., deflazacort, dexamethasone and methylprednisolone).

In a specific embodiment, stabilized antibodies administered to an animal are of a species origin or species reactivity that is the same species as that of the animal. Thus, in a preferred embodiment, stabilized human or humanized antibodies, or nucleic acids encoding human or humanized stabilized antibodies, are administered to a human patient for therapy or prophylaxis.

In preferred embodiments, immunoglobulins having extended storage stability and/or in vivo half-lives are used in passive immunotherapy (for either therapy or prophylaxis). Because of the extended shelf-life and/or in vivo half-life, passive immunotherapy or prophylaxis can be accomplished using lower doses and/or less frequent administration of the therapeutic resulting in fewer side effects, better patient compliance, less costly therapy/prophylaxis, etc. In a preferred embodiment, the therapeutic/prophylactic is a stabilized antibody that binds RSV, for example, a stabilized form of SYNAGIS® or other anti-RSV antibody. Such anti-RSV antibodies, and methods of administration are disclosed in U.S. patent application Ser. Nos. 09/724,396 and 09/724,531, both entitled "Methods of Administering/Dosing Anti-RSV Antibodies For Prophylaxis and Treatment," both by Young et al., both filed Nov. 28, 2000, and continuation-in-part applications of these applications, Ser. Nos. 09/996,265 and 09/996, 288, respectively, entitled "Methods of Administering/Dosing Anti-RSV Antibodies for Prophylaxis and Treatment," by Young et al., all which are incorporated by reference herein in their entireties. Also included are the stabilized anti-RSV antibodies described in Section 5.1, supra.

5.8. Administration of Stabilized Glycoproteins

The invention provides methods of treatment, prophylaxis, and amelioration of one or more symptoms associated with a disease, disorder or infection by administrating to a subject of an effective amount of a stabilized glycoprotein the invention, for example a stabilized antibody of the invention, or pharmaceutical composition comprising a stabilized antibody of the invention, for example a pharmaceutical composition comprising a stabilized antibody of the invention. The invention also provides methods of treatment, prophylaxis, and amelioration of one or more symptoms associated with a disease, disorder or infection by administering to a subject an effective amount of a stabilized glycoprotein of the invention, or a pharmaceutical composition comprising a stabilized glycoprotein of the invention. In a preferred aspect, a stabilized glycoprotein that is administered to a subject is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as a cynomolgous monkey and a human). In a preferred embodiment, the subject is a human.

Various delivery systems are known and can be used to administer a stabilized glycoprotein of the invention, e.g., encapsulation in liposomes, microparticles, microcapsules, recombinant cells capable of expressing the stabilized glycoprotein, receptor-mediated endocytosis (see, e.g., Wu and Wu, *J. Biol. Chem.*, 262:4429-4432, 1987), construction of a nucleic acid as part of a retroviral or other vector, etc. Methods of administering a stabilized glycoprotein, or pharmaceutical composition comprising a stabilized glycoprotein include, but are not limited to, parenteral administration (e.g., intradermal, intramuscular, intraperitoneal, intravenous and subcutaneous), epidural, and mucosal (e.g., intranasal and oral routes). In a specific embodiment, stabilized glycoproteins or pharmaceutical compositions comprising stabilized glycoproteins are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety. In a preferred embodiment, a stabilized glycoprotein or a pharmaceutical composition comprising a stabilized glycoprotein is administered using Alkermes AIR™ pulmonary drug delivery technology (Alkermes, Inc., Cambridge, Mass.).

The invention also provides that a stabilized glycoprotein is packaged in a hermetically sealed container such as an ampoule or sachette indicating the quantity of the stabilized glycoprotein. In one embodiment, the stabilized glycoprotein is supplied as a dry sterilized lyophilized powder or water free concentrate in a hermetically sealed container and can be reconstituted, e.g., with water or saline to the appropriate concentration for administration to a subject. Preferably, the stabilized glycoprotein is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized glycoprotein should be stored at between 2 and 8° C. in its original container and the stabilized glycoprotein should be administered within 12 hours, preferably within 6 hours, within 5 hours, within 3 hours, or within 1 hour after being reconstituted. In an alternative embodiment, a stabilized glycoprotein is supplied in liquid form in a hermetically sealed container indicating the quantity and concentration of the stabilized glycoprotein. Preferably, the liquid form of the stabilized glycoprotein is supplied in a hermetically sealed container at least 1 mg/ml, more preferably at least 2.5 mg/ml, at least 5 mg/ml, at least 8 mg/ml, at least 10 mg/ml, at least 15 mg/kg, or at least 25 mg/ml.

In a specific embodiment, it may be desirable to administer the pharmaceutical compositions comprising the stabilized glycoproteins of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a stabilized glycoprotein, care must be taken to use materials to which the stabilized glycoprotein does not absorb.

In another embodiment, the composition comprising a stabilized glycoprotein can be delivered in a vesicle, in particular a liposome (see Langer, *Science*, 249:1527-1533, 1990; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the composition comprising a stabilized glycoprotein can be delivered in a controlled release or sustained release system. Any technique known to one of skill in the art can be used to produce sustained release formulations comprising one or more stabilized glycoproteins and optionally additional therapeutic molecules. See, e.g., U.S. Pat. No. 4,526,938; PCT publication WO 91/05548; PCT publication WO 96/20698; Ning et al., "Intratumoral Radioimmunotheraphy of a Human Colon Cancer Xenograft Using a Sustained-Release Gel," *Radiotherapy & Oncology*, 39:179-189, 1996; Song et al., "Antibody Mediated Lung Targeting of Long-Circulating Emulsions," *PDA Journal of Pharmaceutical Science & Technology*, 50:372-397, 1995; Cleek et al., "Biodegradable Polymeric Carriers for a bFGF Antibody for Cardiovascular Application," *Pro. Intl. Symp. Control. Rel. Bioact. Mater.*, 24:853-854, 1997; and Lam et al., "Microencapsulation of Recombinant Humanized Monoclonal Antibody for Local Delivery," *Proc. Int'l. Symp. Control Rel. Bioact. Mater.*, 24:759-760, 1997, each of which is incorporated herein by reference in its entirety. In one embodiment, a pump may be used in a controlled release system (see Langer, supra; Sefton, *CRC Crit. Ref. Biomed. Eng.*, 14:20, 1987; Buchwald et al., *Surgery*, 88:507, 1980; and Saudek et al., *N. Engl. J. Med.*, 321:574, 1989). In another embodiment, polymeric materials can be used to achieve controlled release of stabilized glycoproteins (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, *J., Macromol. Sci. Rev. Macromol. Chem.*, 23:61, 1983; see also Levy et al., *Science*, 228:190, 1985; During et al., *Ann. Neurol.*, 25:351, 1989; Howard et al., *J. Neurosurg.*, 71:105, 1989); U.S. Pat. Nos. 5,679,377; 5,916,597; 5,912,015; 5,989,463; 5,128,326; PCT Publication No. WO 99/15154; and PCT Publication No. WO 99/20253). In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)).

Other controlled release systems are discussed in the review by Langer, *Science*, 249:1527-1533, 1990).

In a specific embodiment where the composition of the invention is a nucleic acid encoding a stabilized glycoprotein, the nucleic acid can be administered in vivo to promote expression of its encoded stabilized glycoprotein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA*, 88:1864-1868, 1991), etc. Alternatively, a nucleic acid can be introduced intracellularly and incorporated within host cell DNA for expression by homologous recombination.

The present invention also provides pharmaceutical compositions. Such compositions comprise a prophylactically or therapeutically effective amount of a stabilized glycoprotein and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's complete and incomplete, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of the stabilized glycoprotein, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, prevention or amelioration of one or more symptoms associated with a disease, disorder, or infection can be determined by standard clinical techniques. The precise dose to be employed in the formulation will depend on the route of administration, the age of the subject, and the seriousness of the disease, disorder, or infection, and should be decided according to the judgment of the practitioner and each patient's circumstances. Effective doses may be extrapolated from dose-response curves derived from in vitro or animal model (e.g., the cotton rat or Cynomolgous monkey) test systems.

For stabilized antibodies, the therapeutically or prophylactically effective dosage administered to a subject ranges from about 0.001 to 200 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. In a specific embodiment, the therapeutically or prophylactically effective dosage of a stabilized antibody administered to a subject is typically 0.1 mg/kg to of the subject's body weight. The dosage will, however, depend upon the extent to which the shelf-life and/or in vivo half-life of the molecule has been increased Generally, stabilized human glycoproteins, e.g., stabilized human antibodies, have longer half-lives within the human body than antibodies from other species due to the immune response to the foreign polypeptides. Thus, lower dosages of stabilized human glycoproteins less frequent administration is often possible. Further, the dosage and frequency of administration of stabilized glycoproteins may be reduced also by enhancing uptake and tissue penetration (e.g., into the lung) of the stabilized glycoproteins by modifications such as, for example, lipidation.

Treatment of a subject with a therapeutically or prophylactically effective amount of a stabilized glycoprotein can include a single treatment or, preferably, can include a series of treatments. In a preferred example, a subject is treated with a stabilized glycoprotein in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical composition of the invention is administered once a day, twice a day, or three times a day. In other embodiments, the pharmaceutical composition is administered once a week, twice a week, once every two weeks, once a month, once every six weeks, once every two months, twice a year or once per year. It will also be appreciated that the effective dosage of the stabilized glycoprotein used for treatment may increase or decrease over the course of a particular treatment.

5.9. Gene Therapy

In a specific embodiment, nucleic acids comprising sequences encoding stabilized glycoproteins, are administered to treat, prevent or ameliorate one or more symptoms associated with a disease, disorder, or infection, by way of gene therapy. Gene therapy refers to therapy performed by the administration to a subject of an expressed or expressible nucleic acid. In this embodiment of the invention, the nucleic acids produce their encoded stabilized glycoprotein that mediates a therapeutic or prophylactic effect.

Any of the methods for gene therapy available in the art can be used according to the present invention. Exemplary methods are described below.

For general reviews of the methods of gene therapy, see Goldspiel et al., *Clinical Pharmacy*, 12:488-505, 1993; Wu and Wu, *Biotherapy*, 3:87-95, 1991; Tolstoshev, *Ann. Rev. Pharmacol. Toxicol.*, 32:573-596, 1993; Mulligan, *Science*, 260:926-932, 1993; and Morgan and Anderson, *Ann. Rev.* biochem. 62:191-217, 1993; *TIBTECH* 11(5):155-215, 1993. Methods commonly known in the art of recombinant DNA technology which can be used are described in Ausubel et al. (eds.), Current Protocols in Molecular Biology, John Wiley & Sons, New York (1993); and Kriegler, Gene Transfer and Expression, A Laboratory Manual, Stockton Press, New York (1990).

In a preferred aspect, a composition of the invention comprises nucleic acids encoding a stabilized antibody, said nucleic acids being part of an expression vector that expresses the antibody in a suitable host. In particular, such nucleic acids have promoters, preferably heterologous promoters, operably linked to the stabilized antibody coding region, said promoter being inducible or constitutive, and, optionally, tissue-specific. In another particular embodiment, nucleic acid molecules are used in which the stabilized antibody coding sequences and any other desired sequences are flanked by regions that promote homologous recombination at a desired site in the genome, thus providing for intrachromosomal expression of the antibody encoding nucleic acids (Koller and Smithies, *Proc. Natl. Acad. Sci. USA*, 86:8932-8935, 1989; and Zijlstra et al., *Nature*, 342:435-438, 1989).

In another preferred aspect, a composition of the invention comprises nucleic acids encoding a stabilized glycoprotein, said nucleic acids being a part of an expression vector that expresses the stabilized glycoprotein in a suitable host. In particular, such nucleic acids have promoters, preferably heterologous promoters, operably linked to the coding region of a stabilized glycoprotein, said promoter being inducible or constitutive, and optionally, tissue-specific. In another particular embodiment, nucleic acid molecules are used in which the coding sequence of the stabilized glycoprotein and any other desired sequences are flanked by regions that promote homologous recombination at a desired site in the genome, thus providing for intrachromosomal expression of the glycoprotein-encoding nucleic acids.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retroviral or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.*, 262:4429-4432, 1987) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO 92/20316; WO 93/14188; WO 93/20221). Alternatively, the nucleic acid can be introduced intracellularly and incorporated within host cell DNA for expression, by homologous recombination (Koller and Smithies, *Proc. Natl. Acad. Sci. USA*, 86:8932-8935, 1989; and Zijlstra et al., *Nature*, 342:435-438, 1989).

In a specific embodiment, viral vectors that contain nucleic acid sequences encoding a stabilized glycoprotein are used. For example, a retroviral vector can be used (see Miller et al., *Meth. Enzymol.*, 217:581-599, 1993). These retroviral vectors contain the components necessary for the correct packaging of the viral genome and integration into the host cell DNA. The nucleic acid sequences encoding the stabilized glycoprotein to be used in gene therapy are cloned into one or more vectors, which facilitates delivery of the nucleotide sequence into a subject. More detail about retroviral vectors can be found in Boesen et al., *Biotherapy,* 6:291-302, 1994, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., *J. Clin. Invest.,* 93:644-651, 1994; Klein et al., Blood 83:1467-1473, 1994; Salmons and Gunzberg, *Human Gene Therapy,* 4:129-141, 1993; and Grossman and Wilson, *Curr. Opin. in Genetics and Devel.,* 3:110-114, 1993.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development,* 3:499-503, 1993, present a review of adenovirus-based gene therapy. Bout et al., *Human Gene Therapy,* 5:3-10, 1994, demonstrated the use of adenovirus vectors to transfer genes to the respiratory epithelia of rhesus monkeys. Other instances of the use of adenoviruses in gene therapy can be found in Rosenfeld et al., *Science,* 252:431-434, 1991; Rosenfeld et al., *Cell,* 68:143-155, 1992; Mastrangeli et al., *J. Clin. Invest.,* 91:225-234, 1993; PCT Publication WO 94/12649; and Wang et al., *Gene Therapy,* 2:775-783, 1995. In a preferred embodiment, adenovirus vectors are used.

Adeno-associated virus (AAV) has also been proposed for use in gene therapy (see, e.g., Walsh et al., *Proc. Soc. Exp. Biol. Med.,* 204:289-300, 1993, and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this embodiment, the nucleic acid encoding the stabilized glycoprotein is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcellmediated gene transfer, spheroplast fusion, etc. Numerous techniques are known in the art for the introduction of foreign genes into cells (see, e.g., Loeffler and Behr, *Meth. Enzymol.,* 217:599-618, 1993; Cohen et al., *Meth. Enzymol.,* 217:618-644, 1993; and *Clin. Pharma. Ther.,* 29:69-92, 1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a subject by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the subject.

In an embodiment in which recombinant cells are used in gene therapy, nucleic acid sequences encoding stabilized glycoprotein are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g., PCT Publication WO 94/08598; Stemple and Anderson, *Cell,* 7 1:973-985, 1992; Rheinwald, *Meth. Cell Bio.,* 21A:229, 1980; and Pittelkow and Scott, *Mayo Clinic Proc.,* 61:771, 1986).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

5.10. Characterization and Demonstration of Therapeutic or Prophylactic Utility

Stabilized glycoproteins of the present invention may be characterized in a variety of ways. In particular, the stabilized glycoproteins of the inventions may be characterized in any manner that is suitable for the characterization of the non-stabilized counterparts of the glycoproteins.

Stabilized glycoproteins that are antibodies may be assayed for the ability to immunospecifically bind to an antigen. Such an assay may be performed in solution (e.g., Houghten, *Bio/Techniques,* 13:412-421, 1992), on beads (Lam, *Nature,* 354:82-84, 1991, on chips (Fodor, *Nature,* 364:555-556, 1993), on bacteria (U.S. Pat. No. 5,223,409), on spores (U.S. Pat. Nos. 5,571,698; 5,403,484; and 5,223,409), on plasmids (Cull et al., *Proc. Natl. Acad. Sci. USA,* 89:1865-1869, 1992) or on phage (Scott and Smith, *Science,* 249:386-390, 1990; Devlin, *Science,* 249:404-406, 1990; Cwirla et al., *Proc. Natl. Acad. Sci. USA,* 87:6378-6382, 1990; and Felici, *J. Mol. Biol.,* 222:301-310, 1991) (each of these references is incorporated herein in its entirety by reference). Stabilized antibodies that have been identified to immunospecifically bind to an antigen or a fragment thereof can then be assayed for their specificity affinity for the antigen.

The stabilized antibodies of the invention thereof may be assayed for immunospecific binding to an antigen and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 40° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}$P or $^{125}$I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of the present invention or a fragment thereof for the antigen and the binding off-rates can be determined from the saturation data by scatchard analysis. Competition with a second antibody can also be determined using radioimmunoassays. In this case, the antigen is incubated with an antibody of the present invention or a fragment thereof conjugated to a labeled compound (e.g., $^{3}H$ or $^{125}I$) in the presence of increasing amounts of an unlabeled second antibody.

In a preferred embodiment, BIAcore kinetic analysis is used to determine the binding on and off rates of antibodies to an antigen. BIAcore kinetic analysis comprises analyzing the binding and dissociation of an antigen from chips with immobilized antibodies on their surface (see the Example section infra).

The stabilized antibodies can also be assayed for their ability to inhibit the binding of an antigen to its host cell receptor using techniques known to those of skill in the art. For example, cells expressing the receptor for a viral antigen can be contacted with virus in the presence or absence of a stabilized antibody and the ability of the antibody to inhibit viral antigen's binding can measured by, for example, flow cytometry or a scintillation counter. The antigen or the stabilized antibody can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an and its host cell receptor. Alternatively, the ability of stabilized antibodies to inhibit an antigen from binding to its receptor can be determined in cell-free assays. For example, virus or a viral antigen (e.g., RSV F glycoprotein) can be contacted in a cell-free assay with an antibody and the ability of the antibody to inhibit the virus or the viral antigen from binding to its host cell receptor can be determined. Preferably, the stabilized antibody is immobilized on a solid support and the antigen is labeled with a detectable compound. Alternatively, the antigen is immobilized on a solid support and the antibody is labeled with a detectable compound. The antigen may be partially or completely purified (e.g., partially or completely free of other polypeptides) or part of a cell lysate. Further, the antigen may be a fusion protein comprising the viral antigen and a domain such as glutathionine-S-transferase. Alternatively, an antigen can be biotinylated using techniques well known to those of skill in the art (e.g., biotinylation kit, Pierce Chemicals; Rockford, Ill.).

The stabilized glycoproteins of the invention can also be assayed for their ability to inhibit or downregulate viral or bacterial replication using techniques known to those of skill in the art. For example, viral replication can be assayed by a plaque assay such as described, e.g., by Johnson et al., *Journal of Infectious Diseases,* 176:1215-1224, 1997. The stabilized glycoproteins of the invention of the invention can also be assayed for their ability to inhibit or downregulate the expression of viral or bacterial polypeptides. Techniques known to those of skill in the art, including, but not limited to, Western blot analysis, Northern blot analysis, and RT-PCR, can be used to measure the expression of viral or bacterial polypeptides. Further, the stabilized glycoproteins of the invention of the invention can be assayed for their ability to prevent the formation of syncytia.

The stabilized glycoproteins and compositions comprising the stabilized glycoproteins of the invention are preferably tested in vitro, and then in vivo for the desired therapeutic or prophylactic activity, prior to use in humans. For example, in vitro assays which can be used to determine whether administration of a specific stabilized glycoprotein or stabilized glycoprotein-containing composition is indicated, include in vitro cell culture assays in which a subject tissue sample is grown in culture, and exposed to or otherwise administered a stabilized glycoprotein or stabilized glycoprotein-containing composition, and the effect of such a glycoprotein or composition upon the tissue sample is observed. In various specific embodiments, in vitro assays can be carried out with representative cells of cell types involved in a disease or disorder, to determine if stabilized glycoprotein or composition comprising the stabilized glycoprotein has a desired effect upon such cell types. Preferably, the stabilized glycoproteins are also tested in in vitro assays and animal model systems prior to administration to humans.

The stabilized glycoproteins or compositions comprising the stabilized glycoproteins of the present invention for use in therapy can be tested for their toxicity in suitable animal model systems, including but not limited to rats, mice, cows, monkeys, and rabbits. For in vivo testing for the toxicity of an antibody, a fusion protein, a conjugated molecule, or a composition, any animal model system known in the art may be used.

Efficacy in treating or preventing viral infection may be demonstrated by detecting the ability of a stabilized glycoprotein or composition comprising a stabilized glycoprotein of the present invention to inhibit the replication of the virus, to inhibit transmission or prevent the virus from establishing itself in its host, or to prevent, ameliorate or alleviate one or more symptoms associated with viral infection. The treatment is considered therapeutic if there is, for example, a reduction is viral load, amelioration of one or more symptoms or a decrease in mortality and/or morbidity following administration of an antibody, a fusion protein, a conjugated molecule, or a composition of the invention. The stabilized glycoproteins or compositions comprising the stabilized glycoproteins of the present invention of the invention can also be tested for their ability to inhibit viral replication or reduce viral load in in vitro and in vivo assays.

Efficacy in treating or preventing bacterial infection may be demonstrated by detecting the ability of a stabilized glycoprotein or composition comprising a stabilized glycoprotein of the invention to inhibit the bacterial replication, or to prevent, ameliorate or alleviate one or more symptoms associated with bacterial infection. The treatment is considered therapeutic if there is, for example, a reduction is bacterial numbers, amelioration of one or more symptoms or a decrease in mortality and/or morbidity following administration of the stabilized glycoprotein or composition comprising the stabilized glycoprotein of the invention.

Efficacy in treating cancer may be demonstrated by detecting the ability of a stabilized glycoprotein or composition comprising a stabilized glycoprotein of the invention to inhibit or reduce the growth or metastasis of cancerous cells or to ameliorate or alleviate one or more symptoms associated with cancer. The treatment is considered therapeutic if there is, for example, a reduction in the growth or metastasis of cancerous cells, amelioration of one or more symptoms associated with cancer, or a decrease in mortality and/or morbidity following administration of a stabilized glycoprotein or composition comprising a stabilized glycoprotein of the invention. Stabilized glycoproteins or compositions comprising the stabilized glycoproteins of the invention can be tested for their ability to reduce tumor formation in in vitro, ex vivo, and in vivo assays.

Efficacy in treating inflammatory disorders may be demonstrated by detecting the ability of a stabilized glycoprotein or composition comprising a stabilized glycoprotein of the invention of the invention to reduce or inhibit the inflammation in an animal or to ameliorate or alleviate one or more symptoms associated with an inflammatory disorder. The treatment is considered therapeutic if there is, for example, a reduction is in inflammation or amelioration of one or more symptoms following administration of a stabilized glycoprotein or composition comprising a stabilized glycoprotein of the invention.

Stabilized glycoproteins or compositions comprising the stabilized glycoproteins of the invention can be tested in vitro and in vivo for the ability to induce the expression of cytokines (e.g., IFN-α, IFN-β, IFN-γ, IL-2, IL-3, IL-4, IL-5, IL-6, IL10, IL-12, and IL-15) and activation markers (e.g., CD28, ICOS, and SLAM). Techniques known to those of skill in the art can be used to measure the level of expression of cytokines and activation markers. For example, the level of expression of cytokines can be measured by analyzing the level of RNA of cytokines by, for example, RT-PCR and Northern blot analysis, and by analyzing the level of cytokines by, for example, immunoprecipitation followed by Western blot analysis or ELISA.

Stabilized glycoproteins or compositions comprising the stabilized glycoproteins of the invention of the invention can be tested in vitro and in vivo for their ability to modulate the biological activity of immune cells, preferably human immune cells (e.g., T-cells, B-cells, and Natural Killer cells). The ability of a stabilized glycoprotein or composition comprising a stabilized glycoprotein of the invention to modulate the biological activity of immune cells can be assessed by detecting the expression of antigens, detecting the proliferation of immune cells, detecting the activation of signaling molecules, detecting the effector function of immune cells, or detecting the differentiation of immune cells. Techniques known to those of skill in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as Western blots, immunohistochemistry, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays and FACS analysis. The activation of signaling molecules can be assayed, for example, by kinase assays and electrophoretic shift assays (EMSAs).

Stabilized glycoproteins or compositions comprising the stabilized glycoproteins of the invention can also be tested for their ability to increase the survival period of animals, preferably mammals and most preferably humans, suffering from a disease, disorder, or infection by at least 25%, preferably at least 50%, at least 60%, at least 75%, at least 85%, at least 95%, or at least 99%. Further, stabilized glycoproteins or compositions comprising the stabilized glycoproteins of the invention can be tested for their ability reduce the hospitalization period of animals, preferably mammals and most preferably humans, suffering from a disease, disorder, or infection by at least 60%, preferably at least 75%, at least 85%, at least 95%, or at least 99%. Techniques known to those of skill in the art can be used to analyze the function of the stabilized glycoproteins or compositions comprising the stabilized glycoproteins of the invention in vivo.

5.11. Diagnostic Uses of Stabilized Glycoproteins

Labeled stabilized glycoproteins or compositions comprising the stabilized glycoproteins of the invention can be used for diagnostic purposes to detect, diagnose, or monitor diseases, disorders or infections. The invention provides for the detection or diagnosis of a disease, disorder or infection, comprising: (a) assaying the expression of an antigen in cells or a tissue sample of a subject using one or more stabilized glycoproteins, for example, stabilized antibodies, that bind to the antigen; and (b) comparing the level of the antigen with a control level, e.g., levels in normal tissue samples, whereby an increase in the assayed level of antigen compared to the control level of the antigen is indicative of the disease, disorder or infection.

Stabilized glycoproteins, including antibodies, of the invention can be used to assay antigen levels in a biological sample using classical immunohistological methods as described herein or as known to those of skill in the art (e.g., see Jalkanen et al., *J. Cell. Biol.*, 101:976-985, 1985; Jalkanen et al., *J. Cell. Biol.*, 105:3087-3096, 1987). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, alkaline phosphatase, glucose oxidase; radioisotopes, such as iodine ($^{125}$I, $^{131}$I), carbon ($^{14}$C), sulfur ($^{35}$S), tritium ($^3$H), indium ($^{121}$In), and technetium ($^{99m}$Tc); luminescent labels, such as luminol; and fluorescent labels, such as fluorescein and rhodamine.

One aspect of the invention is the detection and diagnosis of a disease, disorder, or infection in a human. In one embodiment, diagnosis comprises: a) administering (for example, parenterally, subcutaneously, or intraperitoneally) to a subject an effective amount of a labeled stabilized glycoprotein (e.g., antibody) that binds to an antigen; b) waiting for a time interval following the administration for permitting the labeled glycoprotein to preferentially concentrate at sites in the subject where the antigen is expressed (and for unbound labeled molecule to be cleared to background level); c) determining background level; and d) detecting the labeled stabilized glycoprotein in the subject, such that detection of labeled stabilized glycoprotein above the background level indicates that the subject has the disease, disorder, or infection. In accordance with this embodiment, the stabilized glycoprotein is labeled with an imaging moiety which is detectable using an imaging system known to one of skill in the art. Background level can be determined by various methods including, comparing the amount of labeled glycoprotein detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments," Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In one embodiment, monitoring of a disease, disorder or infection is carried out by repeating the method for diagnosing the disease, disorder or infection, for example, one month after initial diagnosis, six months after initial diagnosis, one year after initial diagnosis, etc.

Presence of the labeled glycoproteins can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the glycoprotein is labeled with a radioisotope and is detected in the patient using a radiation responsive surgical instrument (Thurston et al., U.S. Pat. No. 5,441,050). In another embodiment, the glycoprotein is labeled with a fluorescent compound and is detected in the patient using a fluorescence responsive scanning instrument. In another embodiment, the glycoprotein is labeled with a positron emitting metal and is detected in the patient using positron emission-tomography. In yet another embodiment, the glycoprotein is labeled with a paramagnetic label and is detected in a patient using magnetic resonance imaging (MRI).

5.12. Kits

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises a stabilized glycoprotein, including but not limited to a stabilized antibody or immunoglobulin, of the invention, preferably in a purified form, in one or more containers. In a specific embodiment, the kits of the present invention which contain a stabilized antibody or immunoglobulin further contain a substantially isolated antigen as a control. Preferably, the kits of the present invention that comprise a stabilized antibody or immunoglobulin further comprise a control antibody or immunoglobulin which does not react with the antigen included in the kit. In another specific embodiment, the kits of the present invention contain a means for detecting the binding of a stabilized antibody or immunoglobulin to an antigen (e.g., the stabilized antibody or immunoglobulin may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized antigen. The antigen provided in the kit may also be attached to a solid support. In a more specific embodiment the detecting means of the above-described kit includes a solid support to which antigen is attached. Such a kit may also include a non-attached reporter-labeled anti-human antibody. In this embodiment, binding of the stabilized antibody or immunoglobulin to the antigen can be detected by binding of the said reporter-labeled antibody.

6. EXAMPLES 6.1. Materials and Methods 6.1.1. Sample Preparation

The MAbs were heated at 55° C. for one week, filtered with 0.45 μm membrane filter (Millipore Corporation, Amicon, Ultrafree-MC), fractionated with SEC (Toso-Haas G3000SW$_{XL}$ column, 7.8×300 mm) under isocratic elution (0.7 mL/min) with 0.1 M di-sodium phosphate containing 0.1 M sodium sulfate and 0.05% sodium azide, and detected at 280 nm (FIG. 1). Two fractions of interest, 'Peak 1' and 'Peak 2', were collected for further characterization.

6.1.2. Sample Cleaning for MALDI-TOF-MS

Samples were diluted with HPLC water (1:10) in a centrifuge filter unit (Millipore Corporation, MICROCON YM-30, Regenerated Cellulose 30,000 MWCO), mixed by gentle pipetting, and centrifuged at 12,500 RPM (14,300×g) for 2 minutes.

6.1.3. MALDI-TOF-MS

MALDI-TOF-MS data was acquired on a Kratos Kompact MALDI I instrument in linear positive mode with a typical mass accuracy of 0.5%. The sample (0.3 μL) was deposited onto a MALDI target and mixed with sinapinic acid matrix solution (0.3 μL, 40 mg/mL in water/acetonitrile/TFA, 50/50/0.1, v/v/v) and dried under ambient temperature. Each spectrum is the average of 50 shots.

6.1.4. Off-Slide Reduction for MALDI-TOF-MS

Samples (1 μL) for reduction were mixed with 1 μL of freshly prepared reducing solution (3.3 mg/mL DTT in 50 mM Tris buffer, pH 8.2) in a 500 μL microfuge tube and incubated for at least 30 minutes, prior to analysis by MALDI-TOF-MS.

6.1.5. Deglycosylation with N-Glycanase

Samples were digested with N-Glycanase (0.9 mU N-Glycanase, GLYKO) at 37° C. for 20-23 hours in 50 mM Tris buffer, pH 8.2. As a control, the non-heated reference standard (30 μL, approximately 2 mg/mL) was digested with N-Glycanase (9.0 mU N-Glycanase) in the same way, simultaneously.

6.1.6. Reduction and Alkylation for LC-ESI-MS

The deglycosylated sample (7.5 μL, approximately 0.2 mg/mL) was mixed with 42.5 μL of reducing buffer (2.5 mg/mL DTT, 6 M Guanindine, pH 8.2) and kept in a 56° C. water bath for 60 minutes. 4-Vinylpyridine (0.5 μL) was added to the sample and kept at ambient temperature for 30 minutes. After that, the reduced and alkylated sample was immediately loaded onto a reversed phase C4 column (Phenomenex Jupiter 5 μm C4, 300 Å, 250×2.0 mm), and isolated from the reactants and analyzed with LC-ESI-MS.

6.1.7. LC-ESI-MS with LCQduo Ion Trap Mass Spectrometer

The deglycosylated, reduced, and alkylated samples were isolated from the reactants and fractionated using a reversed phase column (Phenomenex Jupiter 5 μm C4, 300 Å, 250×2.0 mm) with a binary gradient HPLC system (Agilent 1100) by a linear gradient of 30-50% acetonitrile in water, both with 0.1% trifluroacetic acid, over 16 min. The flow rate through column was 200 μL/min. The sample eluting from the reversed phase column was directed to a UV detector, then split 1:1, one half going to the switching valve on the LCQduo Ion Trap mass spectrometer (ThermoFinnigan, San Jose, Calif.), the remaining half to waste. The switching valve diverted the flow to the LCQduo ion-trap mass spectrometer, or to waste.

The ESI-MS data was acquired in positive full scan mode on the LCQduo ion trap mass spectrometer. The BioWorks 1.0 deconvolution program (ThermoFinnigan) was used to reconstruct the mass spectra.

6.2. Results 6.2.1. MALDI-TOF-MS of 'Peak 1'

In order to obtain suitable accuracy, multiple measurements were carried out for MALDI-TOF-MS analysis (Tables 1 and 2). Therefore, the molecular weight shown in the MALDI-TOF-MS mass spectra (FIGS. 2, 3, 4, and 5) is a single measurement and not the same as the mean value of the multiple measurements shown in Tables 1 and 2. One component (101090 Da) identified in 'Peak 1' has a molecular weight consistent with the molecular size estimated by SEC. After deglycosylation, the molecular weight decreased by 3312 Da, compared with that of the non-deglycosylated 'Peak 1'. This indicates that N-linked oligosaccharides are attached to the SEC fraction 'Peak 1' (FIG. 2).

After reduction, three components were observed for both the deglycosylated and the non-deglycosylated 'Peak 1' (FIG. 3). The molecular masses of the light chain (L) did not change significantly after deglycosylation, consistent with no N-linked oligosaccharides in it (FIG. 3 and Table 1). After deglycosylation, however, the molecular masses for both heavy chain (H) and C-terminal fragment of heavy chain (H frag) decreased by 1658 and 1637 Da, respectively. The total mass change (3295 Da) for both heavy chain and C-terminal fragment of heavy chain after reduction is very close to the mass change (3312 Da) prior to the reduction (Table 1). This indicates that both the heavy chain and the C-terminal fragment of the heavy chain in 'Peak 1' have a single N-linked oligosaccharide moiety. Taken together, our results shows that 'Peak 1' is composed of a light chain, a heavy chain, a heavy chain C-terminal fragment, and two N-linked oligosaccharide moieties.

6.2.2. MALDI-TOF-MS of 'Peak 2'

One component with molecular weight of 47686, consistent with the molecular size estimated by SEC, was identified in 'Peak 2'. The molecular weight did not change significantly after deglycosylation (FIG. 4 and Table 2). This indicates that no N-linked oligosaccharide is present in 'Peak 2'.

The dominant singly-protonated molecular ion of the reduced 'Peak 2' has half the mass of that of the non-reduced 'Peak 2', as shown in FIGS. 4 and 5 and Table 2. It demonstrated that 'Peak 2' is composed of two parts, linked by disulfide bond(s), with a molecular mass very close to that of the light chain. 'Peak 1' consists of the light chain, heavy chain, and C-terminal fragment of the heavy chain, and two N-linked oligosaccharides, as discussed above. Therefore, it is very likely that 'Peak 2' (47686 Da) is composed of a light chain and an N-terminal fragment of the heavy chain. The N-terminal fragment of the heavy chain has a very close molecular weight to that of the light chain. Thus, the MALDI-TOF-MS data suggested that the MAb A is cleaved in the hinge region of one of the two heavy chains. A similar result was obtained for a different MAb B (data not included).

6.2.3. RP-HPLC of 'Peak 1' and 'Peak 2'

On-line LC-ESI-MS analysis was carried out on the deglycosylated, reduced, and alkylated 'Peak 1' and 'Peak 2'. Analysis of the non-heated MAb reference standard served as a control to assure that no artificial modification was introduced to the analytes during deglycosylation, reduction, and alkylation and that all three reaction steps were carried out under the appropriate experimental conditions.

Five fractions ('1-A', '1-B', '1-C', '1-D', and '1-E') were observed in the RP-HPLC UV chromatogram for 'Peak 1' and four fractions ('2-A', '2-B', '2-C', and '2-D') for 'Peak 2' (FIG. 6). Comparing with the retention time of the heavy chain and light chain observed in the RP-HPLC UV chromatogram of the non-heated reference standard, it is obvious that the '1-B', '1-C', and '1-D' correspond to the C-terminal fragments of the heavy chain, the heavy-chain, and the light-chain, respectively. Similarly, '2-B' and '2-C' correspond to the N-terminal fragments of the heavy chain and the light-chain, respectively. This is consistent with the MALDI-TOF-MS results, described above. A similar result was obtained for 'Peak 1' and 'Peak 2' of the MAb B, (data not included).

6.2.4. ESI-MS of 'Peak 1'

FIG. 7 show the reconstructed mass spectra for the RP-HPLC fractions '1-B', '1-C', '1-D', and '1-E'. The expansion of the reconstructed mass spectrum for FIG. 7a is shown in FIG. 8. No ESI-MS data was acquired for the RP-HPLC fraction '1-A'. The components identified in the RP-HPLC fraction '1-B' are consistent with C-terminal fragments of the heavy chain (FIG. 8 and Table 3). The molecular weights of the components detected in the RP-HPLC fractions '1-C' and '1-D' are consistent with the calculated molecular weights of the heavy chain (50196 Da) and the light chain (24463 Da), respectively (FIGS. 7b and 7c and Table 3).

Similar to the last RP-HPLC fraction of non-heated reference standard, the heavy chain was identified in the RP-HPLC fraction '1-E' (FIG. 7d and Table 3). Neither light chain nor the heavy-chain C-terminal fragments were identified in this fraction. This may be due to the better ionization efficiency of the heavy chain in electrospray ionization process over the light chain and heavy-chain C-terminal fragments. The ionization of the light-chain and the heavy-chain C-terminal fragments might also be suppressed by the heavy chain.

Similar results were obtained for the RP-HPLC fractions '1-B', '1-C', and '1-D' of 'Peak 1' of MAb B (data not included). Fractions '1-B', '1-C', and '1-D' correspond to the heavy-chain C-terminal fragments, heavy-chain, and light-chain, respectively. The heavy chain was also detected in the fraction '1-E'.

6.2.5. ESI-MS of 'Peak 2'

The reconstructed mass spectra for the RP-HPLC fractions '2-B', '2-C', and '2-D' are shown in FIGS. 9. The expansion of the reconstructed mass spectrum (FIG. 9) is shown in FIG. 10. No ESI-MS data was acquired for the RP-HPLC fraction '2-A'. The components identified in the RP-HPLC fraction '2-B' are consistent with the heavy-chain N-terminal fragments (FIG. 10a and Table 4). The N-terminal fragments identified in 'Peak 2' complement very well with the C-terminal fragments found in 'Peak 1'. The molecular weight of the component observed in the RP-HPLC fraction '2-C' is consistent with the calculated molecular weight of the light chain (24463 Da) (FIG. 10b). A small peak with mass 104 Da less than that of the light chain, corresponding to the light chain with one free cysteine, may be due to incomplete alkylation.

The components identified in the RP-HPLC fraction '2-D' include both the light chain and all the N-terminal fragments of the heavy chain observed in the fractions '2-C' and '2-B' (FIG. 10c and Table 4). This suggests that both the light chain and the N-terminal fragments were not completely eluted off the column at the retention times of 19.0 and 20.4 minutes. Remaining portions eluted off the column during a strongly hydrophobic mobile phase (95% acetonitrile) washing. Unlike 'Peak 1', ionization suppression of the light chain and N-terminal fragments by the intact heavy chain did not occur, as the heavy chain was not present in 'Peak 2'.

which are linked by disulfide bonds. The heavy-chain and the heavy-chain C-terminal fragments contained a N-linked oligosaccharide moiety.

Part B ('Peak 2') is composed of the light chain and the N-terminal fragments of the heavy chain, which are linked by disulfide bonds.

Those skilled in the art will recognize, or be able to ascertain using no more routine experimentation, many equivalents to the specific embodiments of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

TABLE 1

Molecular weight analysis of the SEC fraction 'Peak 1' of heat-stressed MAb A with MALDI-TOF-MS.

| | non-reduced | | | | reduced | | |
|---|---|---|---|---|---|---|---|
| treatment | non-deglyco | deglyco | MW diff* | component | non-deglyco | deglyco | MW diff* |
| n | 6 | 6 | | | 7 | 14 | |
| MW (mean) | 101090 | 97778 | 3312 | L | 24107 | 23952 | 155 |
| % cv | 0.19 | 0.17 | | | 0.16 | 0.45 | |
| MW (mean) | | | | H frag | 26725 | 25088 | 1637 |
| % cv | | | | | 0.13 | 0.33 | |
| MW (mean) | | | | H | 50759 | 49101 | 1658 |
| % cv | | | | | 0.11 | 0.32 | |
| total MW | | | | L + H frag + H | 101591 | 98141 | 3450 |

*= (MW of non-deglycosylated) − (MW of deglycosylated), n = number of measurements.
L = light chain, H = heavy chain, H frag = fragment of heavy chain

TABLE 2

Molecular weight analysis of the SEC fraction 'peak 2' of heat-stressed MAb A with MALDI-TOF-MS.

| | non-reduced | | | | reduced | | |
|---|---|---|---|---|---|---|---|
| treatment | non-deglyco | deglyco | MW diff* | component | non-deglyco | deglyco | MW diff* |
| n | 7 | 7 | | | 7 | 14 | |
| MW (mean) | 47686 | 47552 | 134 | L/H frag | 24088 | 23884 | 204 |
| % cv | 0.14 | 0.14 | | | 0.52 | 0.15 | |

*= (MW of non-deglycosylated) − (MW of deglycosylated), n = number of measurements.
L = light chain, H = heavy chain, H frag = fragment of heavy chain.

Similar results were obtained for the RP-HPLC fractions '2-B', '2-C', and '2-D' of 'Peak 2' of MAb B (data not included). Fractions '2-B' and '2-C' correspond to the heavy-chain N-terminal fragments and light chain, respectively. Both the heavy-chain N-terminal fragments and light chain were also detected in the fraction '2-D'.

6.3. Conclusion

MAbs were raggedly cleaved into two parts, A and B, within the hinge region of one of the heavy chains.

Part A ('Peak 1') is composed of the light chain, the heavy chain, and the C-terminal fragments of the heavy chain,

TABLE 3

Components identified in the deglycosylated, reduced, and alkylated SEC fraction 'Peak 1' of heat-stressed MAb A with LC-ESI-MS

| RP-HPLC Fraction | Componet | Sequence | Calculated [MW PEC* + H] | Measured [M + H] | Accuracy |
|---|---|---|---|---|---|
| 1-B | H C-Frag | 222-447 | 26049.64 | 26049 | −0.002% |
| | | 222-447 + O | 26065.64 | 26069 | 0.013% |
| | | 223-447 | 25934.55 | 25935 | 0.002% |
| | | 223-447 + O | 25950.55 | 25952 | 0.006% |
| | | 224-447 | 25806.38 | 25805 | −0.005% |

TABLE 3-continued

Components identified in the deglycosylated, reduced, and alkylated SEC fraction 'Peak 1' of heat-stressed MAb A with LC-ESI-MS

| RP-HPLC Fraction | Componet | Sequence | Calculated [MW PEC* + H] | Measured [M + H] | Accuracy |
|---|---|---|---|---|---|
| | | 225-447 | 25705.27 | 25703 | −0.009% |
| | | 226-447 | 25566.13 | 25568 | 0.007% |
| | | 226-447 + O | 25584.13 | 25584 | −0.001% |
| 1-C | H | 1-447 | 50196.96 | 50196 | −0.002% |
| | | 190-447 | 29732.85 | 29731 | −0.006% |
| 1-D | L | 1-219 | 24463.54 | 24462 | −0.006% |
| | | 8-219 | 23702.67 | 23701 | −0.007% |
| 1-E | H | 1-447 | 50196.96 | 50189 | −0.016% |
| | | 190-447 | 29732.85 | 29733 | 0.001% |

*= molecular weight of the component alkylated with 4-vinylpyridine (pyridylethyl cysteine)

TABLE 4

Components identified in the deglycosylated, reduced, and alkylated SEC fraction 'Peak 2' of heat-stressed MAb A with LC-ESI-MS

| RP-HPLC Fraction | Componet | Sequence | Calculated [MW PEC* + H] | Measured [M + H] | Accuracy |
|---|---|---|---|---|---|
| 2-B | H N-Frag | 1-221 | 24164.35 | 24163 | −0.006% |
| | | 1-222-H2O | 24261.44 | 24259 | −0.010% |
| | | 1-222 | 24279.44 | 24276 | −0.014% |
| | | 1-223 | 24407.61 | 24404 | −0.015% |
| | | 1-224 | 24508.71 | 24505 | −0.015% |
| | | 1-225 | 24645.85 | 24642 | −0.016% |
| | | 1-237 | 26035.56 | 26032 | −0.014% |
| 2-C | L | 1-219 | 24463.54 | 24463 | −0.002% |
| | | 8-219 | 23702.67 | 23704 | 0.006% |
| | | 1-219 w/2 free Cys | 24358.4 | 24359 | 0.002% |
| 2-D | H N-Frag | 1-221 | 24164.35 | 24159 | −0.022% |
| | | 1-222-H2O | 24261.44 | 24258 | −0.014% |
| | | 1-222 | 24279.44 | 24276 | −0.014% |
| | | 1-223 | 24407.61 | 24406 | −0.007% |
| | | 1-224 | 24508.71 | 24509 | 0.001% |
| | | 1-225 | 24645.85 | 24643 | −0.012% |
| | | 1-226 | 24746.96 | 24747 | 1.61636E−06 |
| | | 1-237 | 26035.56 | 26034 | −0.006% |
| | L | 1-219 | 24463.54 | 24463 | −0.002% |
| | | 1-219 w/2 free Cys | 24358.4 | 24357 | −0.006% |

*= molecular weight of the component alkylated with 4-vinylpyridine (pyridylethyl cysteine)

Partial Sequence of the hinge region of MAb A

NH2 -------CDKTHTC ---------COOH-SEQ ID NO.80

What is claimed is:

1. A modified human or humanized IgG1 comprising a modified hinge region containing an amino acid substitution at position cysteine 233 with either alanine, arginine, asparagine, aspartic acid, glutamic acid, glutamine, glycine, histidine, isoleucine, leucine, lysine, methionine, phenylalanine, proline, serine, threonine, tryptophan, tyrosine or valine, as numbered according to Kabat, said modified IgG1 exhibiting reduced degradation upon heating to 55° C. for one week, as determined by mass spectrometry, as compared to a corresponding wild-type IgG1 not comprising said amino acid substitutions.

2. The modified IgG1 of claim 1, wherein said amino acid substitutions further comprise an amino acid substitution at position cysteine 239 with either alanine, arginine, asparagine, aspartic acid, glutamic acid, glutamine, glycine, histidine, isoleucine, leucine, lysine, methionine, phenylalanine, proline, serine, threonine, tryptophan, tyrosine or valine, as numbered according to Kabat.

3. A modified human or humanized IgG1 comprising a modified hinge region containing an amino acid substitution at position cysteine 239 with either alanine, arginine, asparagine, aspartic acid, glutamic acid, glutamine, glycine, histidine, isoleucine, leucine, lysine, methionine, phenylalanine, proline, serine, threonine, tryptophan, tyrosine or valine, as numbered according to Kabat, said modified IgG1 exhibiting reduced degradation upon heating to 55° C. for one week, as determined by mass spectrometry, as compared to a corresponding wild-type IgG1 not comprising said amino acid substitutions.

4. A modified human or humanized IgG1 comprising a modified hinge region containing an amino acid substitution at position aspartic acid 234 with either alanine, arginine, asparagine, cysteine, glutamic acid, glutamine, glycine, histidine, isoleucine, leucine, lysine, methionine, phenylalanine, proline, serine, threonine, tryptophan, tyrosine or valine, as numbered according to Kabat, said modified IgG1 exhibiting reduced degradation upon heating to 55° C. for one week, as determined by mass spectrometry, as compared to a corresponding wild-type IgG1 not comprising said amino acid substitutions.

5. A modified human or humanized IgG1 comprising a modified hinge region containing an amino acid substitution at position lysine 235 with either alanine, arginine, asparagine, aspartic acid, cysteine, glutamic acid, glutamine, glycine, histidine, isoleucine, leucine, methionine, phenylalanine, proline, serine. threonine, tryptophan, tyrosine or valine, as numbered according to Kabat, said modified IgG1 exhibiting reduced degradation upon heating to 55° C. for one week, as determined by mass spectrometry, as compared to a corresponding wild-type IgG1 not comprising said amino acid substitutions.

6. A modified human or humanized IgG1 comprising a modified hinge region containing an amino acid substitution at position threonine 236 with either alanine, arginine, asparagine, aspartic acid, cysteine, glutamic acid, glutamine, glycine, histidine, isoleucine, leucine, methionine, phenylalanine, proline, serine, tryptophan, tyrosine or valine, as numbered according to Kabat, said modified IgG1 exhibiting reduced degradation upon heating to 55° C. for one week, as determined by mass spectrometry, as compared to a corresponding wild-type IgG1 not comprising said amino acid substitutions.

7. A modified human or humanized IgG1 comprising a modified hinge region containing an amino acid substitution at position histidine 237 with either alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine, as numbered according to Kabat, said modified IgG1 exhibiting reduced degradation upon heating to 55° C. for one week, as determined by mass spectrometry, as compared to a corresponding wild-type IgG1 not comprising said amino acid substitutions.

8. The modified IgG1 of claim 7, wherein said amino acid substitution at position histidine 237 is a valine or isoleucine.

9. A modified human or humanized IgG1 comprising a modified hinge region containing an amino acid substitution at position glycine 249 with either alanine, arginine, asparagine, aspartic acid, cysteine, glutamic acid, glutamine, histidine, isoleucine, leucine, lysine, methionine, phenylalanine, proline, serine, threonine, tryptophan, tyrosine, or valine, as numbered according to Kabat, said modified IgG1 exhibiting reduced degradation upon heating to 55° C. for one week, as determined by mass spectrometry, as compared to a corresponding wild-type IgG1 not comprising said amino acid substitution.

10. The modified IgG1 of claim 9, wherein said amino acid substitution at position glycine 249 is a valine or isoleucine.

11. A modified human or humanized IgG4 comprising a modified hinge region containing an amino acid substitution at position serine 236 with proline, as numbered according to Kabat, said modified IgG4 exhibiting reduced degradation upon heating to 55° C. for one week, as determined by mass spectrometry, as compared to a corresponding wild-type IgG4 not comprising said amino acid substitution.

12. A modified human or humanized IgG4 comprising a modified hinge region containing an amino acid substitution at position serine 241 with proline, as numbered according to Kabat, said modified IgG4 exhibiting reduced degradation upon heating to 55° C. for one week, as determined by mass spectrometry, as compared to a corresponding wild-type IgG4 not comprising said amino acid substitution.

* * * * *